(12) United States Patent
Sugiyama

(10) Patent No.: US 7,556,911 B2
(45) Date of Patent: Jul. 7, 2009

(54) TITANOCENE BASED COMPOUND, PHOTOSENSITIVE COMPOSITION, PHOTOSENSITIVE TRANSFER SHEET AND PATTERN FORMING METHOD

(75) Inventor: Takekatsu Sugiyama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 158 days.

(21) Appl. No.: 11/713,014

(22) Filed: Mar. 2, 2007

(65) Prior Publication Data

US 2007/0212642 A1   Sep. 13, 2007

(30) Foreign Application Priority Data

Mar. 3, 2006   (JP)   ............................. 2006-057830

(51) Int. Cl.
   *G03F 7/00*   (2006.01)
   *G03F 7/004*   (2006.01)
(52) U.S. Cl. .............. 430/270.1; 430/281.1; 430/286.1; 526/150; 526/160; 526/352
(58) Field of Classification Search .............. 430/270.1, 430/281.1, 286.1; 526/160, 150, 352
   See application file for complete search history.

(56) References Cited

U.S. PATENT DOCUMENTS 4,590,287 A   5/1986   Riediker et al.

FOREIGN PATENT DOCUMENTS

| EP | 0122223 A2 | | 10/1984 |
|---|---|---|---|
| JP | 59152396 A | * | 8/1984 |
| JP | 63-41483 A | | 2/1988 |
| JP | 63-41484 A | | 2/1988 |
| JP | 02-000249 A | | 1/1990 |
| JP | 02-000291 A | | 1/1990 |
| JP | 03-012403 A | | 1/1991 |
| JP | 03-027393 A | | 2/1991 |

OTHER PUBLICATIONS

Yin, Rongjun; Shein, H., Wang, Q., Zhu, Y. Synthesis and crystal structure studies of titanacyclic compounds. Lanzhou Daxue Zuebao, Ziran Kexueban (1991), 21 (1), 59-64 (abstract shown only).*

L. Summers, et al., Diaryl Bis-(cyclopentadienyl)-titanium Compounds, J. Am. Chem. Soc., Jul. 5, 1955, pp. 3604-3606, vol. 77.

* cited by examiner

*Primary Examiner*—Amanda C. Walke
(74) *Attorney, Agent, or Firm*—Sughrue Mion, PLLC

(57) ABSTRACT

A titanocene compound having a carbonyl group, and a photosensitive composition whose sensitivity has been enhanced by containing this as a photopolymerization initiator, a photosensitive transfer sheet using said photosensitive composition, and a pattern forming method using said photosensitive transfer sheet are provided.

20 Claims, No Drawings

TITANOCENE BASED COMPOUND, PHOTOSENSITIVE COMPOSITION, PHOTOSENSITIVE TRANSFER SHEET AND PATTERN FORMING METHOD

BACKGROUND OF THE INVENTION

1. Field of the Invention

The present invention relates to a titanocene based compound having a carbonyl group, and a photosensitive composition used in the fields of printed wiring boards, lead frames, semiconductor packages, members for a display (e.g., color filters, pillar materials, rib materials, spacers, partition walls), three dimensional optical moldings, image forming materials (e.g., printing matrices, proofs) and pattern formation, using the titanocene based compound as a photopolymerization initiator, a photosensitive transfer sheet using the photosensitive composition, and a pattern forming method using the photosensitive transfer sheet.

2. Description of the Related Art

With highly advanced performances of photosensitive compositions, it is one of regards strongly required to make photosensitivity high. Among them, as a photopolymerization initiator having an absorbance in the range of long wavelengths, for example, a titanocene compound further having a substituent on a fluoroaryl group has been proposed (see European Patent Application Publication No. 12223, Japanese Patent Application Laid-Open (JP-A) No. 63-41483, JP-A No. 63-41484, JP-A No. 02-249, JP-A No. 02-291, JP-A 03-12403, JP-A No. 03-27393 and Summers L. et al., J. Am. Chem. Soc., 77:3604, 1955).

However, it is hard to say that the high photosensitivity has been sufficiently accomplished in the titanocene compound proposed above.

Meanwhile, as methods for synthesizing the titanocene compound linking an aromatic ring, the method employing (1) a step of preparing an aromatic lithium compound or an aromatic Grignard compound and (2) a step of reacting with a titanocene dihalide compound has been known (see Summers L. et al., J. Am. Chem. Soc., 77:3604, 1955).

However, there has been a problem in that the aromatic lithium compound or the aromatic Grignard compound can not be prepared from a raw material having a reactive functional group such as a carbonyl group.

Therefore, no titanocene based compound having the carbonyl group, no photosensitive compound whose sensitivity is enhanced by containing this as the photopolymerization initiator, no photosensitive transfer sheet using the photosensitive composition and no pattern forming method using the photosensitive transfer sheet have been provided yet, and it is an actual circumstance that further improvement and development are desired.

BRIEF SUMMARY OF THE INVENTION

The present invention makes it a task to solve the above conventional various problems and accomplish the following object. That is, it is the object of the present invention to provide a titanocene based compound having a carbonyl group, a photosensitive compound whose sensitivity is enhanced by containing this as the photopolymerization initiator, a photosensitive transfer sheet using the photosensitive composition and a pattern forming method using the photosensitive transfer sheet.

The titanocene based compound of the present invention has the carbonyl group as represented by the following general formula (I), and thus, the sensitivity can be enhanced in the photosensitive composition by containing this as the photopolymerization initiator.

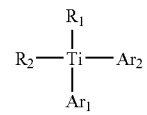

general formula (I)

In the above general formula (I), $R_1$ and $R_2$ each independently represents any of cyclopentadienyl, indenyl and tetrahydroindenyl groups which may have substituents, or may be linked one another via a bivalent linking group. X represents any of a direct bond, an oxygen atom and a sulfur atom, or represents any of chain or cyclic alkylene, alkylidene and arylene groups which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II), or may be linked one another via a bivalent linking group Y. Y represents any of methylene, alkylidene, cycloalkylidene groups, an oxygen atom, a sulfur atom and CO, and when Y is CO, $Ar_1$ and $Ar_2$ need not be substituted with the group represented by the above general formula (II).

general formula (II)

In the above general formula (II), $R_3$ represents any of a hydrogen atom, and alkyl, alkenyl, cycloalkyl, aryl and aralkyl groups which may have substituents, or may be bound to an aromatic ring to form a 5-membered or 6-membered condensed ring containing a carbonyl group.

The photosensitive composition of the present invention can enhance its sensitivity because it contains the titanocene based compound of the present invention.

The photosensitive transfer sheet of the present invention can enhance its sensitivity because it uses the photosensitive composition containing the titanocene based compound of the present invention.

In the pattern forming method of the present invention, the pattern can be efficiently formed because of using the photosensitive transfer sheet of the present invention.

DETAILED DESCRIPTION OF THE INVENTION

The titanocene based compound of the present invention is represented by the following general formula (I).

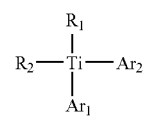

general formula (I)

In the above general formula (I), $R_1$ and $R_2$ each independently represents any of cyclopentadienyl, indenyl and tetrahydroindenyl groups which may have substituents, or may be linked one another via a bivalent linking group. X represents any of a direct bond, an oxygen atom and a sulfur atom, or represents any of chain or cyclic alkylene, alkylidene and arylene groups which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II), or may be linked one another via a bivalent linking group Y. Y represents any of a methylene group, an alkylidene group, a cycloalkylidene group, an oxygen atom, a sulfur atom and CO, and when Y is CO, $Ar_1$ and $Ar_2$ need not be substituted with the group represented by the above general formula (II)

general formula (II)

In the above general formula (II), $R_3$ represents any of a hydrogen atom, and alkyl, alkenyl, cycloalkyl, aryl and aralkyl groups which may have substituents, or may be bound to an aromatic ring to form a 5-membered or 6-membered condensed ring containing the carbonyl group.

The substituents which the cyclopentadienyl, indenyl and tetrahydroindenyl groups in $R_1$ and $R_2$ in the above general formula (I) may have are not particularly limited, and include, for example, alkyl groups having 1 to 18 carbon atoms, alkoxy groups having 1 to 18 carbon atoms, alkenyl groups having 2 to 18 carbon atoms, cycloalkyl groups having 5 to 8 carbon atoms, aryl groups having 6 to 16 carbon atoms, aralkyl groups having 7 to 16 carbon atoms, cyano groups and halogen atoms.

As the above $R_1$ and $R_2$, specifically, cyclopentadienyl, methylcyclopentadienyl and pentamethylcyclopentadienyl groups are preferable, and the cyclopentadienyl group is particularly preferable.

In $R_3$ in the above general formula (II), as the alkyl group for example, those having 1 to 18 carbon atoms are preferable. As the cycloalkyl group, for example, those having 5 to 8 carbon atoms are preferable. As the aryl group, for example, those having 6 to 16 carbon atoms are preferable. As the aralkyl group, for example, those having 7 to 16 carbon atoms are preferable. These may also have the substituent as already described.

The 5-membered or 6-membered condensed ring which the $R_3$ can form include, for example, phenyl rings, naphthalene rings and pyridine rings.

The condensed ring is preferably substituted with fluorine atoms. As the condensed ring substituted with such fluorine atoms, for example, a 5-membered or 6-membered heterocyclic aromatic ring containing a fluorine-substituted phenyl group and one to two heteroatoms, where at least one of ortho positions for the carbon bond with Ti in the above general formula (I) has been substituted with the fluorine atom is preferable. It is more preferable that both the ortho positions have been substituted with the fluorine atoms.

The preferable condensed ring includes, for example, a 2,6-difluorophen-1-yl group and a 2,4-difluoropyridi-3-yl group.

It is preferable that $Ar_1$ and $Ar_2$ in the above general formula (I) are the same group.

It is preferable that in the $Ar_1$, at least one of the ortho positions for the carbon bond with Ti has been substituted with the fluorine atom, and it is preferable that both the ortho positions have been substituted with the fluorine atoms.

In addition to the fluorine atom, the substituents which the $Ar_1$ and $Ar_2$ may have are not particularly limited, and include, for example, alkyl groups having 1 to 18 carbon atoms, alkenyl groups having 2 to 18 carbon atoms, cycloalkyl groups having 5 to 8 carbon atoms, aryl groups having 6 to 12 carbon atoms and aralkyl groups having 7 to 12 carbon atoms.

A carbon atom number in the alkyl group is preferably 1 to 12 and more preferably 1 to 6.

The carbon atom number in the alkenyl group is preferably 2 to 12 and more preferably 2 to 6.

The alkyl groups include specifically, for example, methyl, ethyl, propyl, isopropyl, hexyl, decyl, dodecyl, octadecyl, and alkenyl groups having the carbon atoms corresponding to the above carbon atom number.

The cycloalkyl groups include, for example, cyclopentyl and cyclohexyl groups.

The aryl groups include, for example, phenyl groups, and the aralkyl groups include, for example, benzyl groups.

The compound represented by the above general formula (I) is any one in which, for example, $R_1$ and $R_2$ are selected from cyclopentadienyl and cyclopentadienyl substituted with the alkyl group having 1 to 6 carbon atoms, and is preferably the compound in which $Ar_1$ and $Ar_2$ are represented by the following general formula (V).

As the cyclopentadienyl group substituted with the alkyl group having 1 to 6 carbon atoms in the above $R_1$ and $R_2$, a pentamethylcyclopentadienyl group is more preferable.

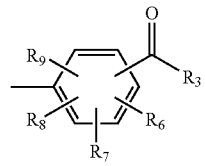

general formula (V)

In the above general formula (V), $R_3$ is the same as defined for $R_3$ in the general formula (II). $R_6$, $R_7$, $R_8$ and $R_9$ each independently represents any of hydrogen atoms or fluorine atoms.

As the above $R_3$, alkyl groups having 1 to 18 carbon atoms, alkenyl groups having 2 to 18 carbon atoms, cycloalkyl groups having 5 to 10 carbon atoms, aryl groups and heteroaryl groups having 6 to 12 carbon atoms, and aralkyl groups having 7 to 12 carbon atoms, which may have substituents in the above general formula (V) are preferable.

As the above alkyl groups, those having 1 to 12 carbon atoms are more preferable, and as the above alkenyl groups, those having 2 to 12 carbon atoms are more preferable.

The substituents which the above $R_3$ has include suitably, for example, hydroxy, alkyloxy, aryloxy, aralkyloxy, alkylthio, arylthio, aralkylthio, acyloxy, sulfonyloxy and aminocarbonyloxy, and more specifically include suitably, for example, methyl, ethyl, propyl, butyl, pentyl, 2-ethylhexyl, decyl, hexadecyl, cyclopentyl, methoxyethyl, ethoxyethyl, methoxypropyl, methylthioethyl, ethylthioethyl, methylthiopropyl, acetoxypropyl, ethoxycarbonylmethyloxymethyl, methanesulfonyloxypropyl, butylaminocarbonyloxypropyl, vinyl, allyl, phenyl, benzyl and naphthyl.

The above $R_6$, $R_7$, $R_8$ and $R_9$ may be hydrogen atoms, but preferably one or more of them are fluorine atoms, and more preferably two or more are the fluorine atoms. It is more preferable that any one of two groups selected from $R_6$, $R_7$, $R_8$ and $R_9$ adjacent to a carbon atom bound to Ti is the fluorine atom, and in particular preferably both are the fluorine atoms.

In the above general formula (V), it is preferable to bind to any position of a meta position and a para position for the carbon atom bound to Ti, and it is more preferable to bind to the meta position.

The specific compounds represented by the above general formula (I) are not particularly limited, and for example, the compounds A-1 to A-51 exemplified below are suitably included.

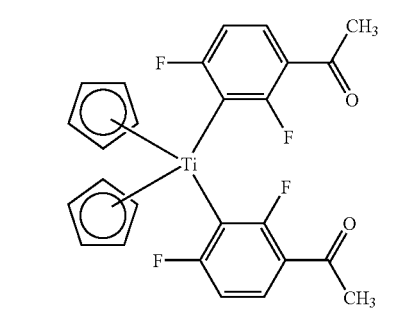
A-1

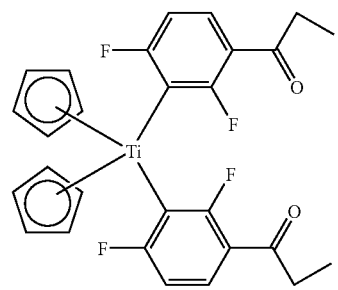
A-2

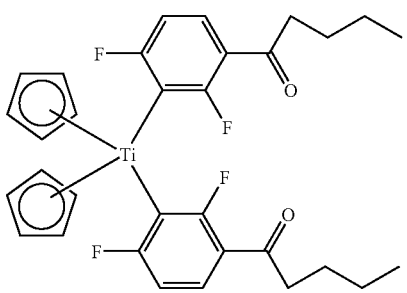
A-3

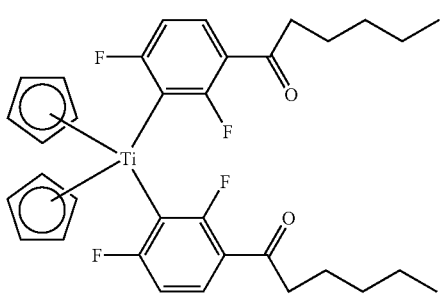
A-4

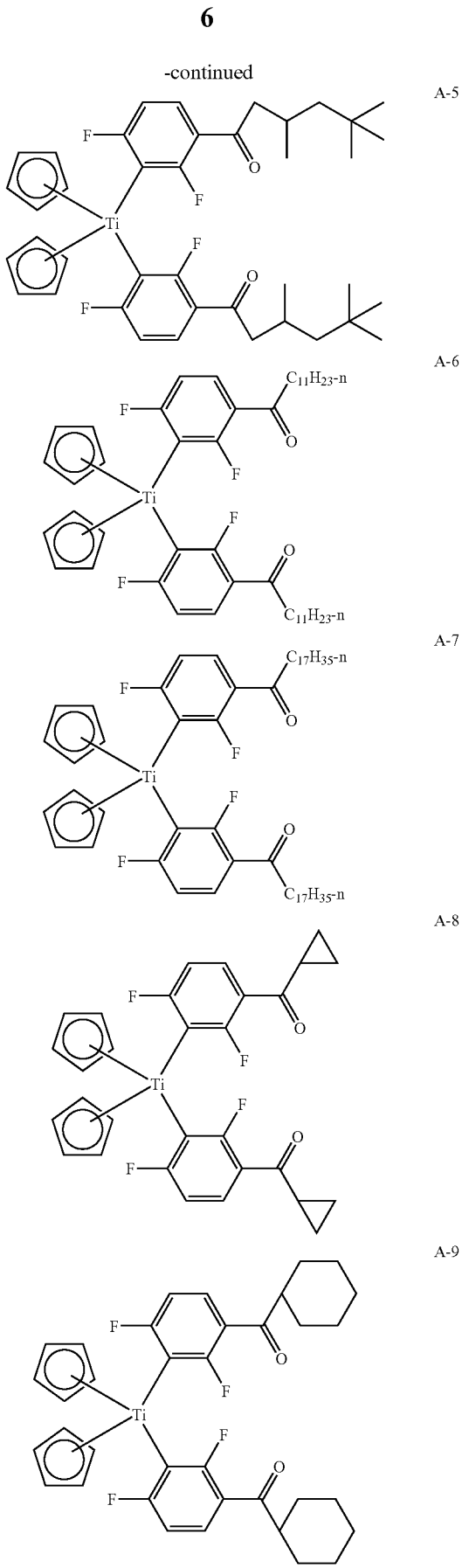

-continued
A-10
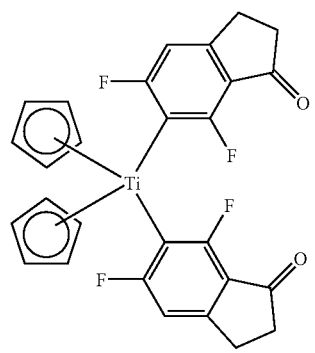
A-11
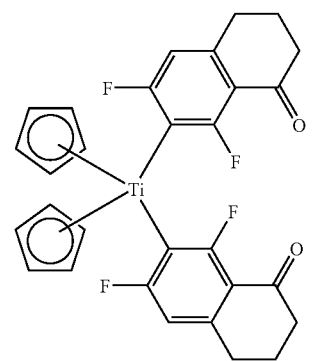
A-12
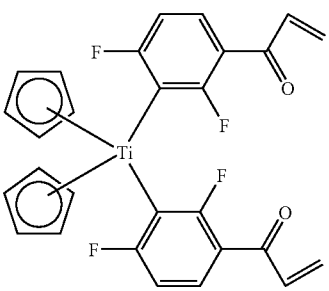
A-13
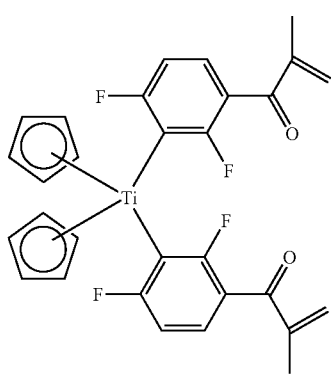
-continued
A-14
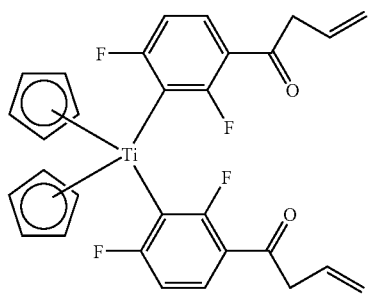
A-15
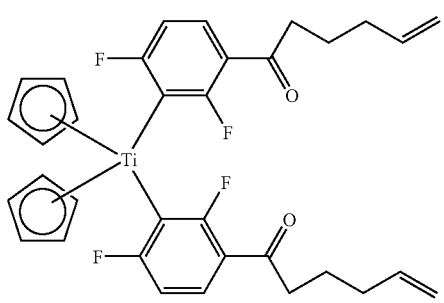
A-16
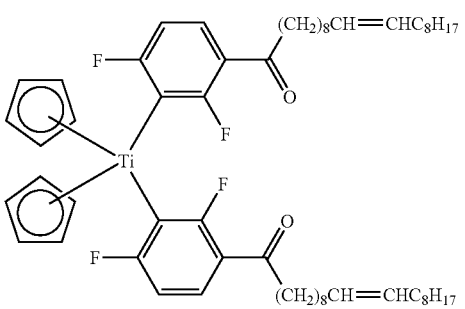
A-17
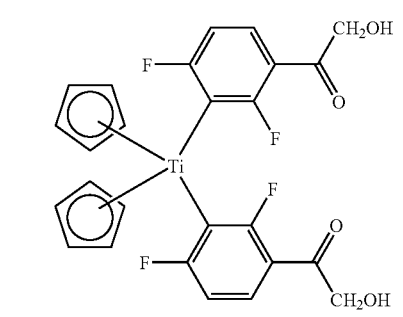
A-18
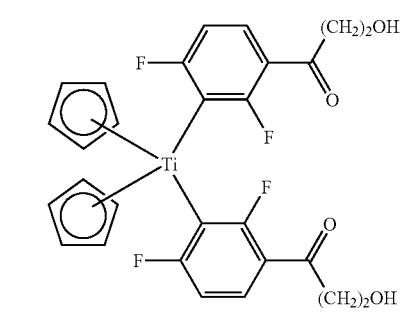

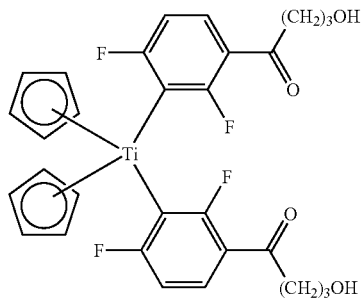
A-19
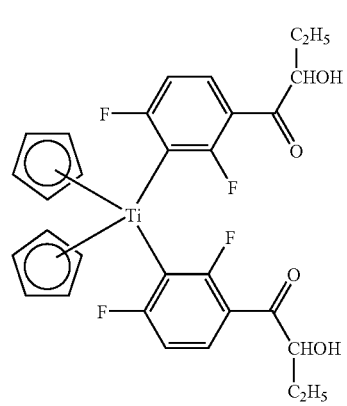
A-20
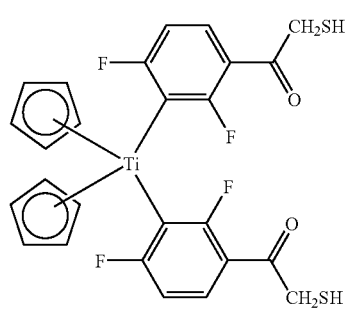
A-21
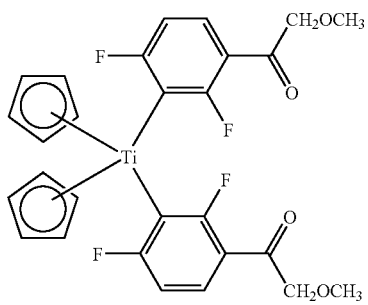
A-22
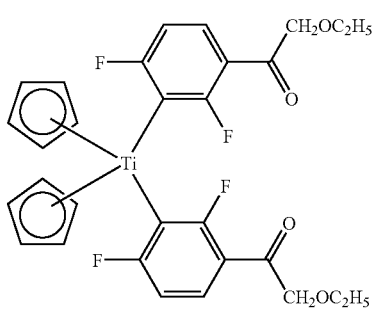
A-23
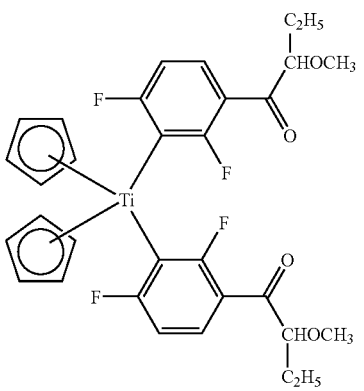
A-24
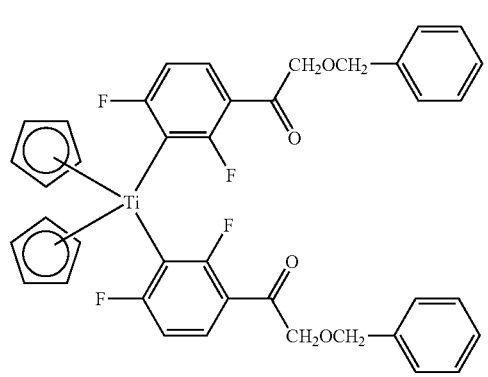
A-25
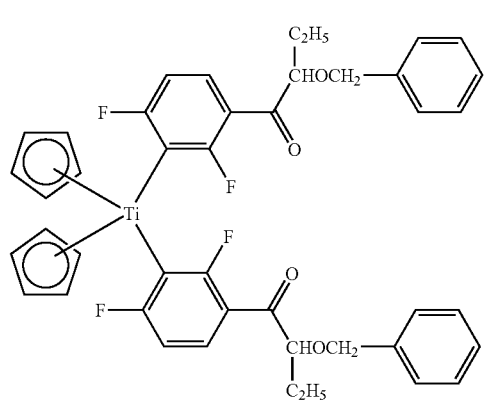
A-26
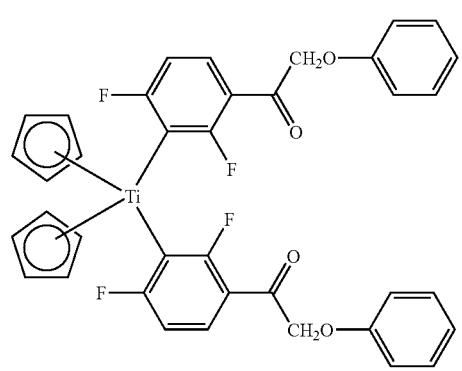
A-27

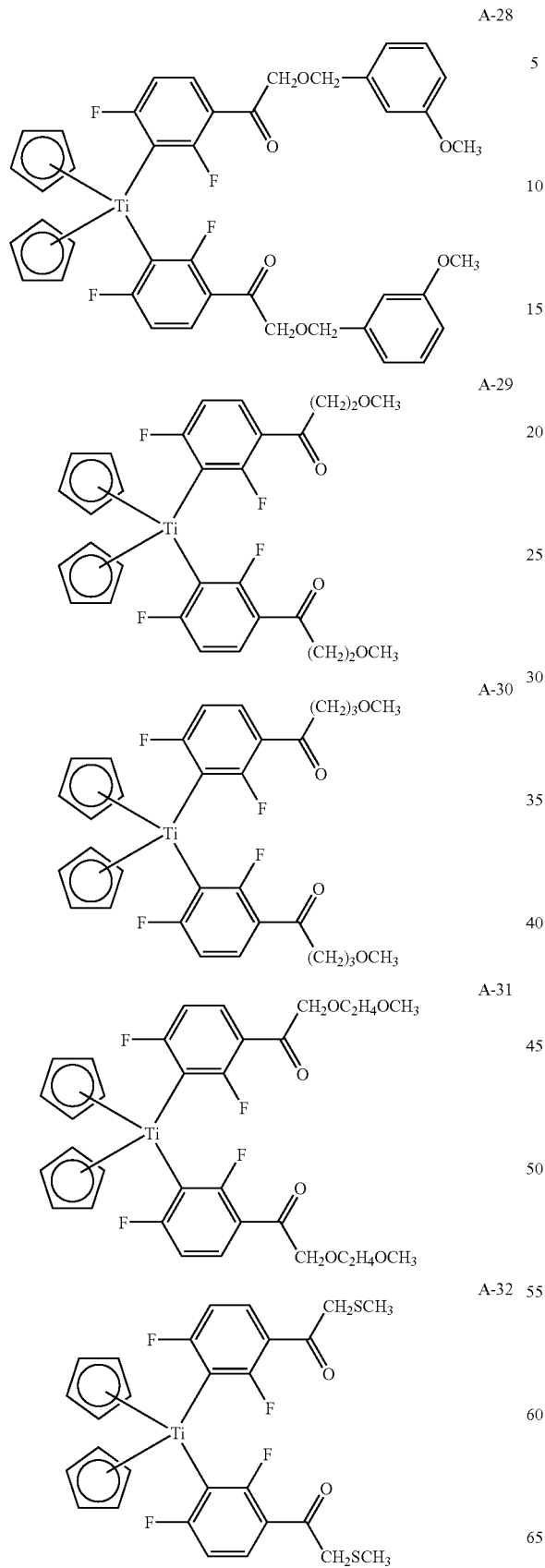
A-28
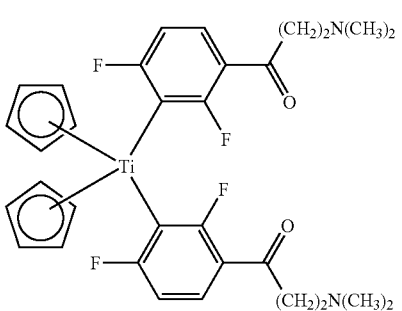
A-33
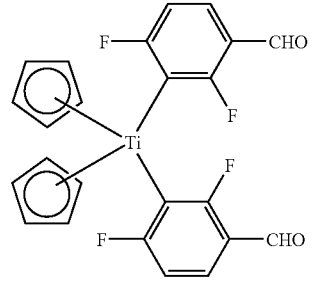
A-34
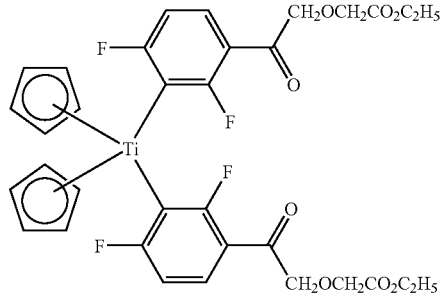
A-35
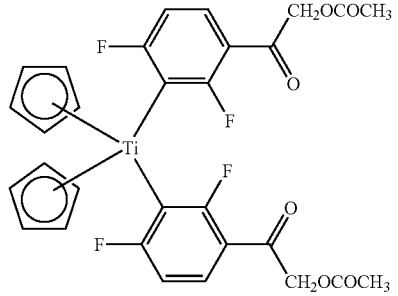
A-36
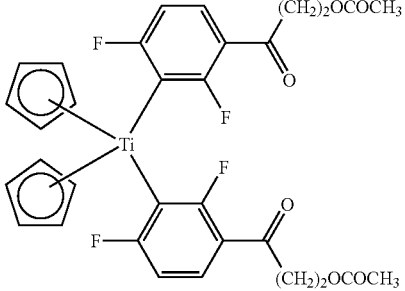
A-37

-continued
A-38
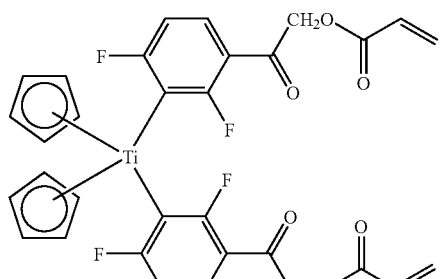
A-39
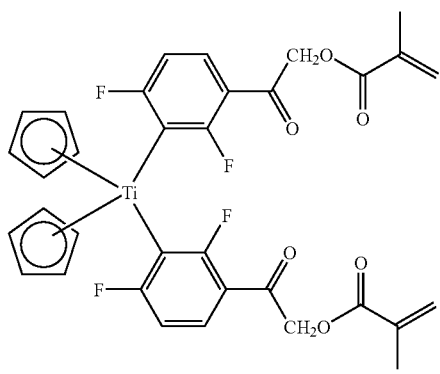
A-40
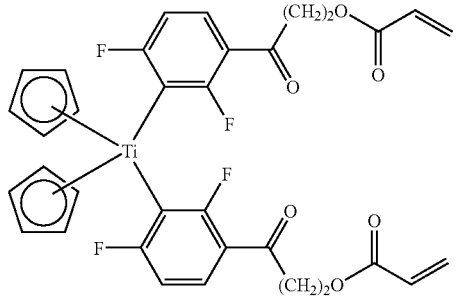
A-41
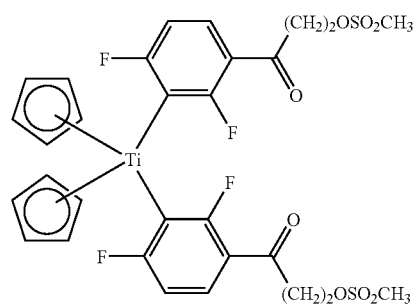
-continued
A-42
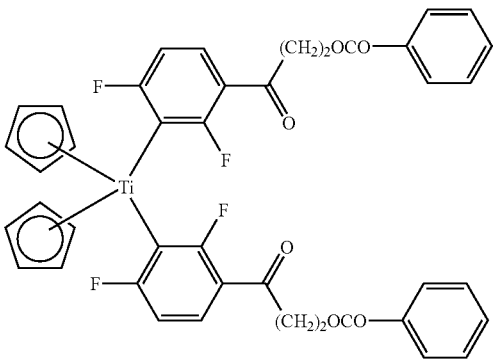
A-43
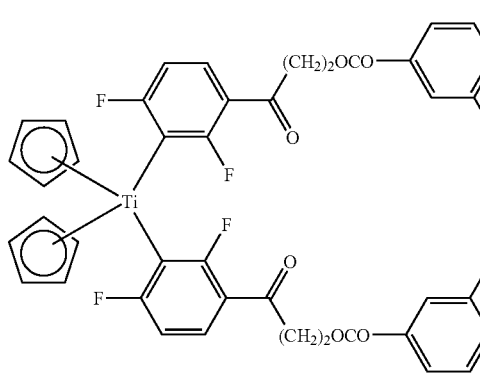
A-44
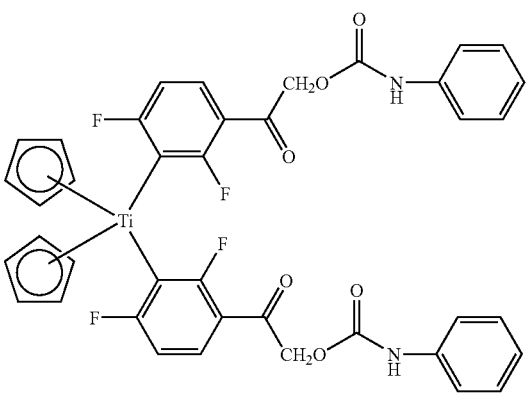
A-45
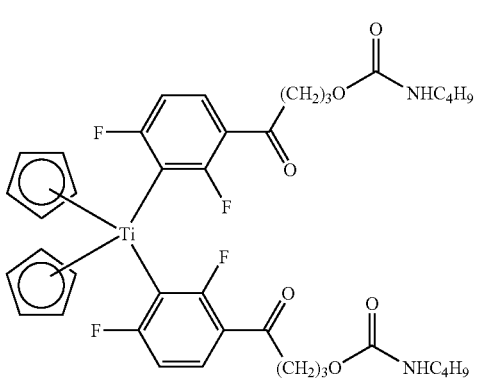

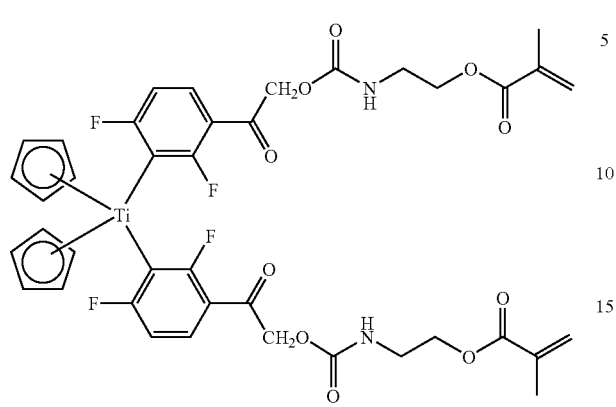
A-46
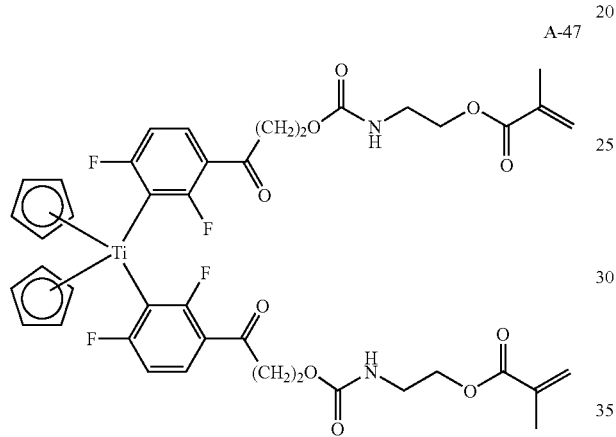
A-47
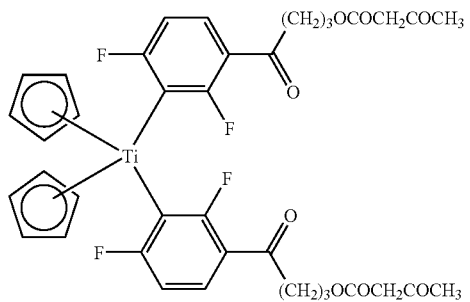
A-48
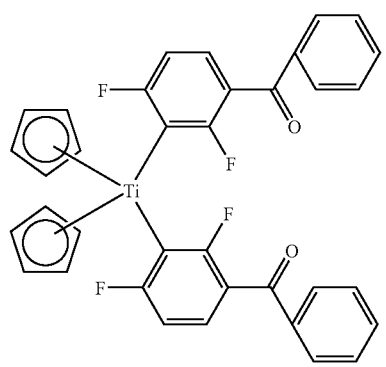
A-49
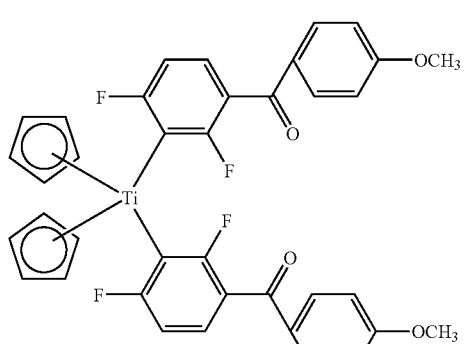
A-50
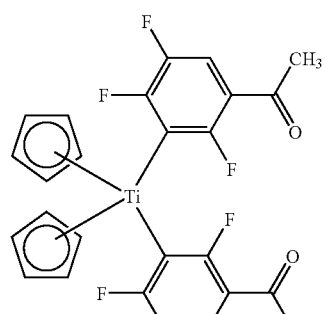
A-51
As the examples having no fluorine atom, the examples having one fluorine atom, the example having three fluorine atoms and the examples having four fluorine atoms, the compounds exemplified below are suitably included.
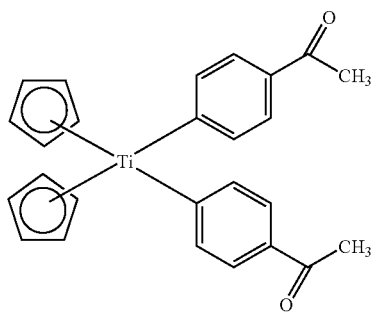
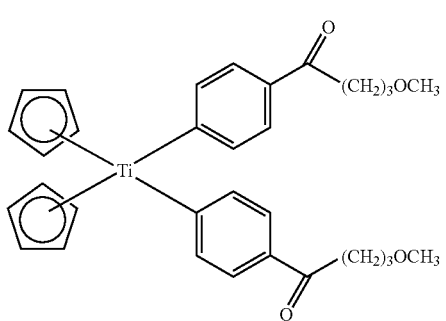

-continued

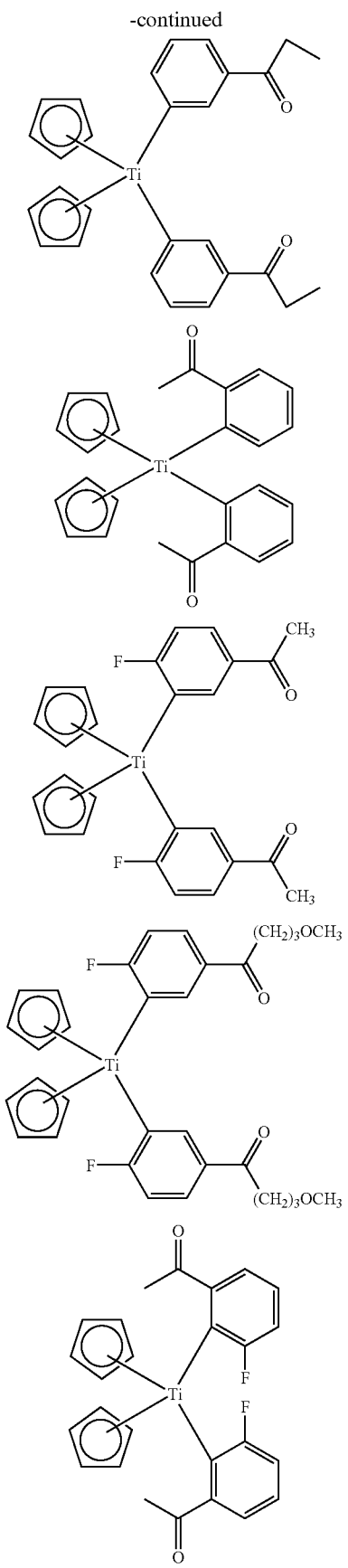

-continued

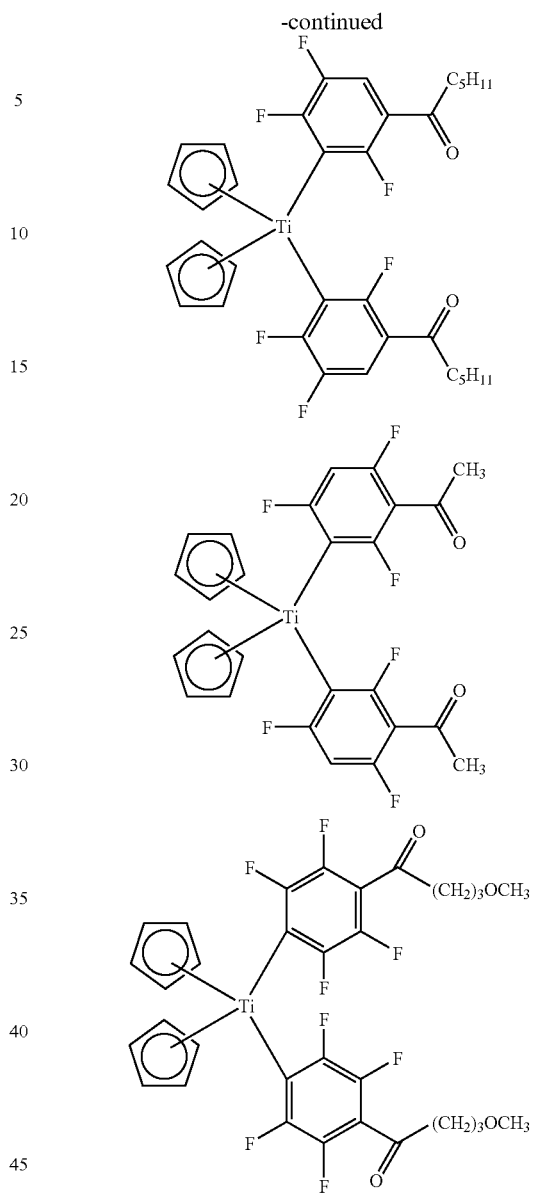

—Production Method—

The method for producing the titanocene based compound of the present invention is not particularly limited as long as the compound represented by the above general formula (I) can be produced, and for example, it is preferable to use the titanocene based compound represented by the following general formula (III) as an intermediate.

general formula (III)

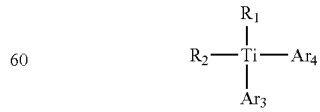

In the above general formula (III), $R_1$ and $R_2$ are the same as defined in the general formula (I). $Ar_3$ and $Ar_4$ each independently represents any of 6-membered carbocyclic, 5-membered heterocyclic and 6-membered heterocyclic aromatic rings in which at least one of the positions other than the position of the carbon atom bound to Ti has been substituted with the group represented by the following general formula (IV).

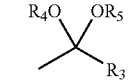

general formula (IV)

In the above general formula (IV), $R_3$ is the same as defined in the general formula (II). $R_4$ and $R_5$ each independently represents alkyl groups having 1 to 5 carbon atoms, or are linked one another to form either a 5-membered ring or a 6-membered ring.

As the above alkyl groups, those having 1 to 3 carbon atoms are preferable, and one carbon atom is particularly preferable.

It is preferable that $Ar_3$ and $Ar_4$ in the above general formula (III) are the same group.

In the above $Ar_3$, at least one of ortho positions for the carbon bond with Ti has been preferably substituted with the fluorine atom, and it is preferable that both the ortho positions have been substituted with the fluorine atoms.

In addition to the fluorine atom, the substituents which the $Ar_3$ and $Ar_4$ may have are not particularly limited, and include, for example, the same substituents as those in $Ar_1$ and $Ar_2$ in the above general formula (I).

The $Ar_3$ and $Ar_4$ are preferably the compounds represented by the above general formula (V).

The specific compounds represented by the above general formula (III) are not particularly limited, and for example, the examples 1 to 6 shown below are suitably included.

example 1

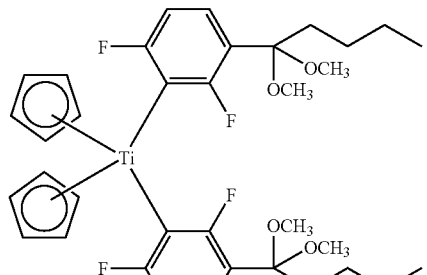

example 3 example 4

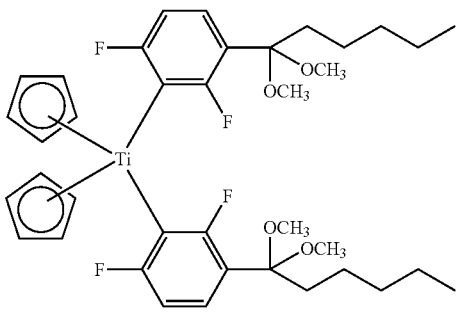

example 5

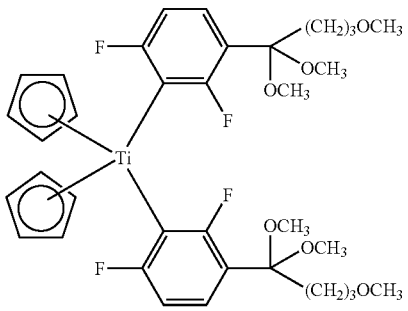

example 6

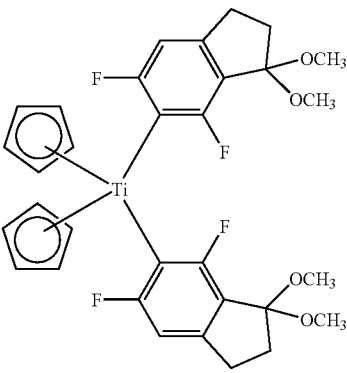

The compound represented by the above general formula (III) is preferable to yield by, for example, reacting the compound represented by the following general formula (VI) with the compound represented by either the following general formula (VII) or (VIII).

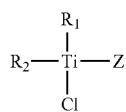

general formula (VI)

-continued

   general formula (VII)

   general formula (VIII)

In the formulae (VI) to (VIII), $R_1$, $R_2$, $Ar_3$ and $Ar_4$ are the same as defined in the general formula (III). M represents any of Li, MgCl, MgBr and MgI. Z represents a halogen atom of Cl, Br and I.

It is preferable that the compound represented by the above general formula (I) is specifically synthesized by the following order of (1) to (4).

(1) The carbonyl group in any of $HAr_1$, $HAr_2$, $XAr_1$ and $XAr_2$ is protected. Here, $Ar_1$ and $Ar_2$ are the same as defined in the above general formula (I), and X represents Cl, Br or I.

(2) The product is converted into the compound represented by either the above general formula (VII) or (VIII).

(3) The compound represented by the above general formula (VI) is further reacted to induce the compound represented by the general formula (III).

(4) The compound represented by the above general formula (I) is yielded by removing the protection.

More specifically, the method comprising a first step of converting the compound represented by the following general formula (IX) into the compound represented by the following general formula (X), a second step of synthesizing the compound represented by the following general formula (XI) using the compound represented by the above general formula (X) as a raw material and a third step of converting the compound represented by the above general formula (XI) into the compound represented by the following structural formula (XII) is suitably included.

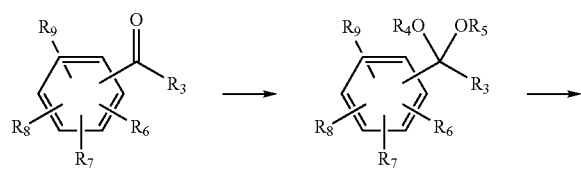

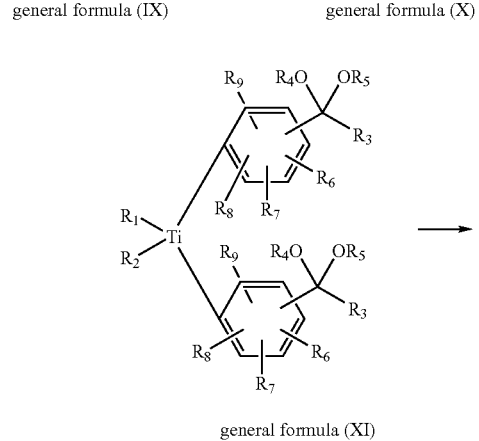

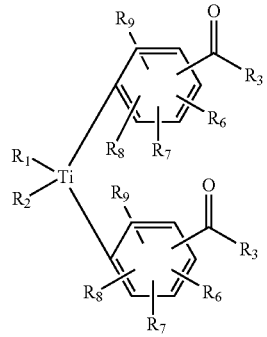

general formula (XII)

In the above general formulae (IX) to (XII), $R_1$ to $R_9$ are the same as defined in the above general formulae (I) to (V).

The above first step is not particularly limited, the method typically used for converting the carbonyl group into an acetal group can be appropriately selected, and for example, the method described in Shin Jikken Kagaku Kouza 14, Synthesis and reaction of organic compounds V, 11-2, Protection of carbonyl group, page 2517, published on Jul. 20, 1978 (edited by the Chemical Society of Japan, Maruzen) is included.

The above second step is not particularly limited, and includes, for example, the method of synthesizing by Friedel-Crafts reaction using carboxylic acid halide which corresponds to 1,3-difluorobenzene.

The above third reaction is not particularly limited, the method typically used for converting the acetal group into the carbonyl group can be appropriately selected, and for example, the method of reproducing the carbonyl group by performing deacetalization under an acidic condition is preferable. In this method, it is preferable to perform the deacetalization at low temperature and for a short time in terms of stabilizing a titanocene skeleton.

A product yielded in above each step can be identified by, for example, a nuclear magnetic resonance apparatus (NMR).

As a specific example of the method for producing the titanocene based compound, the case of the above exemplified compound A-1 will be described below.

(1) Preparation of
1-(1,1-dimethoxy)-2,4-difluorobenzene p-Toluenesulfonic acid is added to and reacted with a solution composed of 2,4-difluoroacetophenone, trimethyl orthoformate and methanol. This is added to an aqueous solution of sodium hydrogen carbonate, which is then extracted with ethyl acetate. An extract is washed with water, dried on $Na_2SO_4$, and ethyl acetate is concentrated under reduced pressure to yield 1-(1,1-dimethoxy)-2,4-difluorobenzene.

(2) Preparation of dicyclopentadienyl-bis{2,6-difluoro-3-(1,1-dimethoxyethyl)phenyl}titanium 1-(1,1-Dimethoxy)-2,4-difluorobenzene was dissolved in diethyl ether, and cooled under nitrogen gas flow. A solution of n-butyl lithium in hexane is added thereto, and stirred at that temperature. Dicyclopentadienyl titanium dichloride is added thereto, and stirred at that temperature. The temperature is gradually raised to room temperature, and the mixture is stirred again at room temperature.

A precipitated precipitate is separated by filtration, this is dissolved in chloroform and insoluble matters are removed by filtration. The solution is concentration under reduced pressure, and a residue is crystallized in ethyl acetate to yield a crystal of dicyclopentadienyl-bis{2,6-difluoro-3-(1,1-dimethoxyethyl)phenyl}titanium.

(3) Preparation of dicyclopentadienyl-bis{2,6-difluoro-3-acetyl)phenyl}titanium (Exemplified Compound A-1)

Dicyclopentadienyl-bis{2,6-difluoro-3-(1,1-dimethoxyethyl)phenyl}titanium is added to a mixed solution of water, glacial acetic acid and ethyl acetate, and stirred at room temperature. Subsequently, the reaction solution is added to an aqueous solution of sodium hydrogen carbonate, which is then extracted with ethyl acetate.

A yielded extract is washed with water, dried on $Na_2SO_4$, and ethyl acetate is concentrated under reduced pressure. Ethanol is added to a residue to crystallize a crystal of dicyclopentadienyl-bis{(2,6-difluoro-3-acetyl)phenyl}titanium (exemplified compound A-1).

Because of having the carbonyl group, the titanocene based compound of the present invention can be suitably used as the photopolymerization initiator in the photosensitive compounds used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs) and pattern forming materials, and can be particularly used suitably for the photosensitive compositions of the present invention.

(Photosensitive Composition)

The photosensitive composition of the present invention comprises a binder, a polymerizable compound and the above titanocene based compound of the present invention as a photopolymerization initiator, and comprises other ingredients appropriately selected if necessary.

—Binder—

As the above binder, it is preferable to be swelling in an alkaline aqueous solution, and it is more preferable to be soluble in the alkaline aqueous solution.

The binder which is swelling or soluble in the alkaline aqueous solution includes suitably, for example, those having an acidic group.

The acidic group is not particularly limited, can be appropriately selected depending on the purpose, includes, for example, carboxyl groups, sulfonic groups and phosphoric groups, and among them, the carboxyl group is preferable.

The binder having the carboxyl group includes, for example, vinyl copolymers, polyurethane resins, polyamide resins and modified epoxy resins having the carboxyl group. Among them, the vinyl copolymer having the carboxyl group is preferable in terms of solubility in an application solvent, solubility in an alkaline developer, synthetic suitability and easy control of a membrane physical property. The copolymer of at least either styrene or a styrene derivative is also preferable in terms of developing property.

The vinyl copolymer having the carboxyl group can be obtained by copolymerization of at least (1) a vinyl monomer having the carboxyl group and (2) a monomer copolymerizable therewith.

The vinyl monomer having the carboxyl group includes, for example, (meth)acrylic acid, vinyl benzoic acid, maleic acid, maleate monoalkyl ester, fumaric acid, itaconic acid, crotonic acid, cinnamic acid, acrylic acid dimer, addition reactants of monomers having hydroxyl group (e.g., 2-hydroxyethyl (meth)acrylate) and a cyclic anhydrate (e.g., maleic acid anhydrate, phthalic acid anhydrate and cyclohexane dicarboxylic acid anhydrate), and ω-carboxy-polycaprolactone mono(meth)acrylate. Among them, (meth)acrylic acid is particularly preferable in terms of copolymerizable property, cost and solubility.

Also as a precursor of the carboxyl group, monomers having the anhydrate such as maleic acid anhydrate, itaconic acid anhydrate and citraconic acid anhydrate may be used.

The other polymerizable monomers are not particularly limited, can be appropriately selected depending on the purpose, and includes, for example, (meth)acrylate esters, crotonate esters, vinyl esters, maleate diesters, fumarate diesters, itaconate diesters, (meth)acrylate amides, vinyl ethers, esters of vinyl alcohol, styrenes (e.g., styrene, styrene derivatives), (meth)acrylonitrile, heterocyclic groups substituted with the vinyl group (e.g., vinyl pyridine, vinyl pyrrolidone, vinyl carbazole), N-vinyl formamide, N-vinyl acetamide, N-vinyl imidazole, vinyl caprolactone, 2-acrylamide-2-methylpropane sulfonic acid, phosphate mono(2-acryloyloxyethyl ester), phosphate mono(1-methyl-2-acryloyloxyethyl ester), and vinyl monomers having a functional group (e.g., urethane, urea, sulfonamide, phenol, imide groups). Among them, the styrenes (e.g., styrene, styrene derivatives) are preferable in terms of being capable of forming permanent patterns such as wiring patterns in high definition and enhancing a tent property of the pattern.

The (meth)acrylate esters include, for example, methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, n-hexyl (meth)acrylate, cyclohexyl (meth)acrylate, t-butylcyclohexyl (meth)acrylate, 2-ethylhexyl (meth)acrylate, t-octyl (meth)acrylate, dodecyl (meth)acrylate, octadecyl (meth)acrylate, acetoxyethyl (meth)acrylate, phenyl (meth)acrylate, 2-hydroxyethyl (meth)acrylate, 2-methoxyethyl (meth)acrylate, 2-ethoxyethyl (meth)acrylate, 2-(2-methoxyethoxy)ethyl (meth)acrylate, 3-phenoxy-2-hydroxypropyl (meth)acrylate, benzyl (meth)acrylate, diethylene glycol monomethyl ether (meth)acrylate, diethylene glycol monoethyl ether (meth)acrylate, diethylene glycol monophenyl (meth)acrylate, triethylene glycol monomethyl ether (meth)acrylate, triethylene glycol monoethyl ether (meth)acrylate, polyethylene glycol monomethyl ether (meth)acrylate, polyethylene glycol monoethyl ether (meth)acrylate, β-phenoxyethoxyethyl acrylate, nonylphenoxy polyethylene glycol (meth)acrylate, dicyclopentanyl (meth)acrylate, dicyclopentenyl (meth)acrylate, dicyclopentenyloxyethyl (meth)acrylate, trifluoroethyl (meth)acrylate, octafluoropentyl (meth)acrylate, perfluorooctylethyl (meth)acrylate, tribromophenyl (meth)acrylate and tribromophenyloxyethyl (meth)acrylate.

The crotonate esters include, for example, butyl crotonate and hexyl crotonate.

The vinyl esters include, for example, vinyl acetate, vinyl propionate, vinyl butyrate, vinyl methoxyacetate and vinyl benzoate.

The maleate diesters include, for example, dimethyl maleate, diethyl maleate and dibutyl maleate.

The fumarate diesters include, for example, dimethyl fumarate, diethyl fumarate and dibutyl fumarate.

The itaconate diesters include, for example, dimethyl itaconate, diethyl itaconate and dibutyl itaconate.

The (meth)acrylamides include, for example, (meth)acrylamide, N-methyl (meth)acrylamide, N-ethyl (meth)acrylamide, N-propyl (meth)acrylamide, N-isopropyl (meth)acrylamide, N-n-butyl acryl(meth)amide, N-t-butyl (meth) acrylamide, N-cyclohexyl (meth)acrylamide, N-(2-methoxyethyl) (meth)acrylamide, N,N-dimethyl (meth)acrylamide, N,N-diethyl (meth)acrylamide, N-phenyl (meth)acrylamide, N-benzyl (meth)acrylamide, (meth)acryloyl morpholine and diacetone acrylamide.

The styrenes include, for example, styrene, methylstyrene, dimethylstyrene, trimethylstyrene, ethylstyrene, isopropylstyrene, butylstyrene, hydroxystyrene, methoxystyrene, butoxystyrene, acetoxystyrene, chlorostyrene, dichlorostyrene, bromostyrene, chloromethylstyrene, hydroxystyrene protected with a group (e.g., t-Boc) capable of being deprotected by an acidic substance, vinylbenzoic acid methyl and α-methylstyrene.

The vinyl ethers include, for example, methyl vinyl ether, butyl vinyl ether, hexyl vinyl ether and methoxyethyl vinyl ether.

The method for synthesizing the vinyl monomer having the functional group includes, for example, an addition reaction of an isocyanate group with a hydroxyl group or an amino group, and specifically includes the addition reaction of a monomer having the isocyanate group with a compound having one hydroxyl group or a compound having one primary or secondary amino group, the addition reaction of the monomer having the hydroxyl group or the monomer having the primary or secondary amino group with monoisocyanate.

The monomer having the isocyanate group includes, for example, the compounds represented by the following structural formulae (1) to (3).

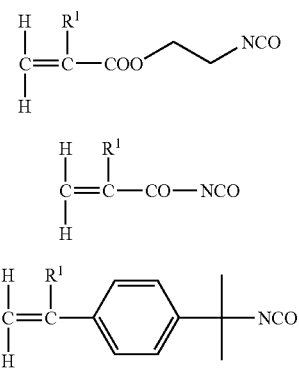

structural formula (1)

structural formula (2)

structural formula (3)

In the above structural formulae (1) to (3), $R^1$ represents a hydrogen atom or a methyl group.

The monoisocyanate includes, for example, cyclohexyl isocyanate, n-butyl isocyanate, toluyl isocyanate, benzyl isocyanate and phenyl isocyanate.

The monomer having the hydroxyl group includes, for example, the compounds represented by the following structural formulae (4) to (12).

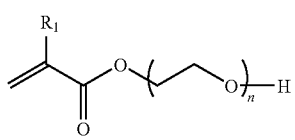

structural formula (4)

-continued

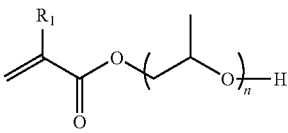

structural formula (5)

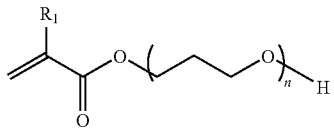

structural formula (6)

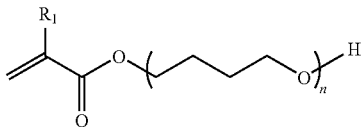

structural formula (7)

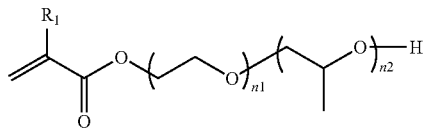

structural formula (8)

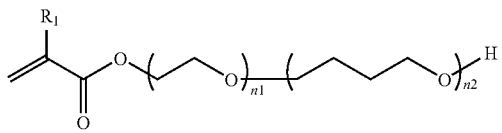

structural formula (9)

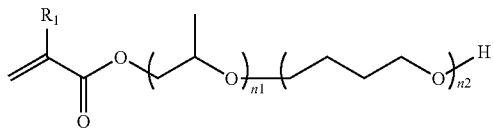

structural formula (10)

structural formula (11)

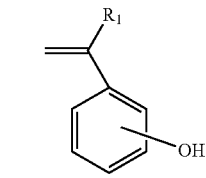

structural formula (12)

In the above structural formulae (4) to (12), $R_1$ represents a hydrogen atom or a methyl group, and n represents an integer of 1 or more.

The compound containing one hydroxyl group includes, for example, alcohols (e.g., methanol, ethanol, n-propanol, i-propanol, n-butanol, sec-butanol, t-butanol, n-hexanol, 2-ethyl hexanol, n-decanol, n-dodecanol, n-octadecanol, cyclopentanol, cyclohexanol, benzyl alcohol and phenylethyl alcohol), phenols (e.g., phenol, cresol and naphthol), and further, as those comprising the substituent, fluoroethanol, trifluoroethanol, methoxyethanol, phenoxyethanol, chlorophenol, dichlorophenol, methoxyphenol and acetoxyphenol are included.

The monomer having the primary or secondary amino group includes, for example, vinyl benzylamine.

The compound having one primary or secondary amino group includes, for example, alkylamine (methylamine, ethylamine, n-propylamine, i-propylamine, n-butylamine, sec-butylamine, t-butylamine, hexylamine, 2-ethylhexylamine, decylamine, dodecylamine, octadecylamine, dimethylamine, diethylamine, dibutylamine and dioctylamine), cyclic alkylamine (cyclopentylamine, cyclohexylamine), aralkylamine (benzylamine, phenetylamine), arylamine (aniline, toluylamine, xylylamine, naphthylamine, and further, combinations thereof N-methyl*N-benzylamine), and amine (trifluoroethylamine, hexafluoroisopropylamine, methoxyaniline and methoxypropylamine) further comprising the substituent.

Other copolymerizable monomers other than the above include suitably, for example, methyl (meth)acrylate, ethyl (meth)acrylate, butyl (meth)acrylate, benzyl (meth)acrylate, 2-ethythexyl (meth)acrylate, styrene, chlorostyrene, bromostyrene and hydroxystyrene.

The other copolymerizable monomers may be used alone or in combination of two or more.

The above vinyl copolymer can be prepared by copolymerizing corresponding monomers by the methods publicly known in accordance with standard methods. For example, it is possible to prepare by taking the method (solution polymerization method) in which the monomers are dissolved in an appropriate solvent and polymerized in the solution by adding the radical polymerization initiator thereto. It is also possible to prepare by taking the method in which the polymerization, so-called emulsification polymerization is performed in a state in which the monomers are dispersed in a water-based vehicle.

The appropriate solvent used in the solution polymerization method is not particularly limited, can be appropriately selected depending on the monomers to be used and the solubility of the copolymer to be produced, and includes, for example, methanol, ethanol, propanol, isopropanol, 1-methoxy-2-propanol, acetone, methyl ethyl ketone, methyl isobutyl ketone, methoxypropyl acetate, ethyl lactate, ethyl acetate, acetonitrile, tetrahydrofuran, dimethylformamide, chloroform and toluene. These solvents may be used alone or in combination of two or more.

The radical polymerization initiator is not particularly limited, and includes, for example, azo compounds such as 2,2'-azobis(isobutyronitrile) (AIBN) and 2,2'-azobis(2,4'-dimethylvaleronitrile), peroxide such as benzoyl peroxide, and persulfate salts such as potassium persulfate and ammonium persulfate.

A content rate of the polymerizable compound having the carboxyl group in the vinyl copolymer is not particularly limited, can be appropriately selected depending on the purpose, and for example, is preferably 5 mol % to 50 mol %, more preferably 10 mol % to 40 mol % and particularly preferably 15 mol % to 35 mol %.

When the content rate is less than 5 mol %, the developing property for an alkaline water is sometimes insufficient, and when it exceeds 50 mol %, developer resistance in a cured portion (image portion) is sometimes insufficient.

A molecular weight of the binder having the carboxyl group is not particularly limited, can be appropriately selected depending on the purpose, and for example, is preferably 2,000 to 300,000 and more preferably 4,000 to 150,000 as a mass average molecular weight.

When the mass average molecular weight is less than 2,000, strength of the membrane becomes easily insufficient and the stable production becomes difficult in some cases. When it exceeds 300,000, the developing property is sometimes reduced.

The binder having the carboxyl group may be used alone or in combination of two or more. The case of combining two or more includes, for example, the combinations of two or more binders composed of different copolymer components, two or more binders having the different mass average molecular weights, and two or more binders having different dispersion degrees.

In the binder having the carboxyl group, a part or all of the carboxyl group may be neutralized with a substrate. The binder may further be combined with the resin such as polyester resins, polyamide resins, polyurethane resins, epoxy resins, polyvinyl alcohol and gelatin having the different structure.

As the binder, it is possible to use the resin soluble in the alkaline aqueous solution described in U.S. Pat. No. 2,873,889.

A content of the binder in the photosensitive composition is not particularly limited, can be appropriately selected depending on the purpose, and for example, is preferably 10% by mass to 90% by mass, more preferably 20% by mass to 80% by mass and particularly preferably 40% by mass to 80% by mass.

When the content is less than 10% by mass, the alkali developing property and adhesiveness to the substrate for forming the printed wiring board (e.g., copper-clad laminate) are sometimes reduced whereas when it exceeds 90% by mass, the stability during the development and the strength of a cured membrane (tent membrane) are sometimes reduced. The content may be the total content of a polymer binding agent combined with the binder as needed.

When the binder has a glass transition temperature (Tg), the glass transition temperature is not particularly limited, can be appropriately selected depending on the purpose, and for example, is preferably 80° C. or above, more preferably 100° C. or above and particularly preferably 120° C. or above in terms of at least any of suppression of tack and edge fusion of the pattern forming materials and enhanced peeling property of the support.

When the glass transition temperature is lower than 80° C., the tack and the edge fusion of a photosensitive transfer sheet described later is sometimes increased, and the peeling property of the a support of the photosensitive transfer sheet is sometimes deteriorated.

An acid value of the binder is not particularly limited, and is preferably 70 mg KOH/g to 250 mg KOH/g, more preferably 90 mg KOH/g to 200 mg KOH/g and particularly preferably 100 mg KOH/g to 180 mg KOH/g.

When the acid value is less than 70 mg KOH/g, the developing property is insufficient, resolution is inferior and the permanent patterns such as wiring patterns can not be obtained in high definition in some cases. When it exceeds 250 mg KOH/g, at least any of the developer resistance and the adhesiveness of the pattern is deteriorated and the permanent patterns such as wiring patterns can not be obtained in high definition in some cases.

—Polymerizable Compound—

The polymerizable compound is not particularly limited, can be appropriately selected depending on the purpose, and suitably includes, for example, monomers and oligomers having at least either an urethane group or an aryl group. It is preferable that these have 2 or more two or more polymerizable groups.

The polymerizable group includes, for example, ethylenic unsaturated bonds (e.g., (meth)acryloyl, (meth)acrylamide, stylyl groups, vinyl groups such as vinyl ester and vinyl ether, allyl groups such as allyl ether and allyl ester), and polymerizable cyclic ether groups (e.g., epoxy, oxetane groups). Among them, the ethylenic unsaturated bond is preferable.

—Monomer Having Urethane Group—

The monomer having the urethane group is not particularly limited as long as the monomer has the urethane group, can be appropriately selected depending on the purpose, and includes for example, the compounds described in Japanese Patent Application Publication (JP-B) No. 48-41708, JP-A No. 51-37193, JP-B No. 05-50737, JP-B No. 07-7208, JP-A No. 2001-154346 and JP-A No. 2001-356476. For example, an adduct of a polyisocyanate compound having two or more isocyanate groups in a molecule and a vinyl monomer having the hydroxyl group in a molecule is included.

The polyisocyanate compound having two or more isocyanate groups in the molecule includes, for example, diisocyanate such as hexamethylene diisocyanate, trimethyl hexamethylene diisocyanate, isophorone diisocyanate, xylene diisocyanate, toluene diisocyanate, phenylene diisocyanate, norbornene diisocyanate, diphenyl diisocyanate, diphenylmethane diisocyanate and 3,3'-dimethyl-4,4'-diphenyl diisocyanate; polyaddition products of the diisocyanate with difunctional alcohol (also in this case, both ends are the isocyanate groups); a buret body of the diisocyanate and a trimer of isocyanurate; adducts of the diisocyanate or diisocyanates with multifunctional alcohol such as trimethylolpropane, pentaerythritol and glycerine or polyfunctional alcohol from which ethylene oxide adducts thereof are obtained.

The vinyl monomer having the hydroxyl group in the molecule includes, for example, 2-hydroxyethyl (meth)acrylate, 2-hydroxypropyl (meth)acrylate, 4-hydroxybutyl (meth)acrylate, diethylene glycol (meth)acrylate, triethylene glycol mono(meth)acrylate, tetraethylene glycol mono(meth)acrylate, octaethylene glycol mono(meth)acrylate, polyethylene glycol mono(meth)acrylate, dipropylene glycol mono(meth)acrylate, tripropylene glycol mono(meth)acrylate, tetrapropylene glycol mono(meth)acrylate, octapropylene glycol mono(meth)acrylate, polypropylene glycol mono(meth)acrylate, dibutylene glycol mono(meth)acrylate, tributylene glycol mono(meth)acrylate, tetrabutylene glycol mono(meth)acrylate, octabutylene glycol mono(meth)acrylate, polybutylene glycol mono(meth)acrylate, trimethylolpropane di(meth)acrylate and pentaerythritol tri(meth)acrylate. One end (meth)acrylate of a diol body having a different alkylene oxide moiety of copolymers (random, block) of ethylene oxide and propylene oxide is also included.

The monomer having the urethane group includes the compounds such as tri((meth)acryloyloxyethyl)isocyanurate, di(meth)acrylized isocyanurate and tri(meth)acrylate of isocyanuric acid modified with ethylene oxide, having an isocyanurate ring. Among them, the compound represented by the following structural formula (13) or (14) is preferable, and it is particularly preferable to contain at least the compound represented by the above structural formula (14) in terms of tent property. These compounds may be used alone or in combination of two or more.

structural formula (13)

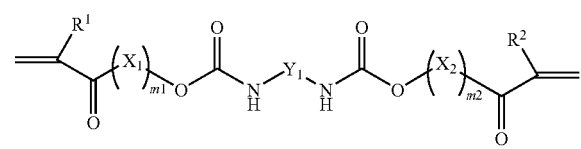

-continued structural formula (14)

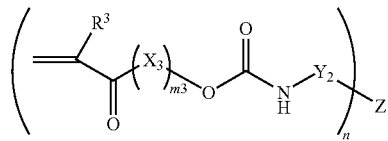

In the above structural formulae (13) and (14), $R^1$ to $R^3$ represent hydrogen atoms or methyl groups. $X_1$ to $X_3$ represent alkylene oxide, and may be used alone or in combination of two or more.

The alkylene oxide group includes suitably, for example, ethylene oxide, propylene oxide, butylene oxide, pentylene oxide, hexylene oxide groups and combined groups thereof (may be combined in random or block). Among them, the ethylene oxide group, the propylene oxide group, the butylene oxide group or the combined group thereof is preferable, and the ethylene oxide group and the propylene oxide group are more preferable.

In the above structural formulae (13) and (14), m1 to m3 represent integers of 1 to 60, preferably 2 to 30 and more preferably 4 to 15.

In the above structural formulae (13) and (14), $Y_1$ and $Y_2$ represent bivalent organic groups having 2 to 30 carbon atoms, include, for example, an alkylene, arylene, alkenylene, alkynylene, carbonyl (—CO—) groups, an oxygen (—O—) atom, a sulfur (—S—) atom, an imino (—NH—) group, a substituted imino group in which a hydrogen atom in the imino group has been substituted with a monovalent hydrocarbon group, a sulfonyl group (—SO$_2$—) or combinations thereof, and among them, the alkylene group, the arylene group and the combinations thereof are preferable.

The alkylene group may have a branched structure or a cyclic structure, and includes, for example, methylene, ethylene, propylene, isopropylene, butylene, isobutylene, pentylene, neopentylene, hexylene, trimethylhexylene, cyclohexylene, heptylene, octylene, 2-ethylhexylene, nonylene, decylene, dodecylene, octadecylene, or any group shown below.

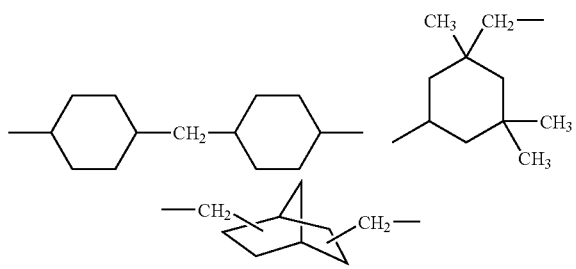

The arylene group may be substituted with a hydrocarbon group, and includes suitably, for example, phenylene, diphenylene, naphthylene groups and the group shown below.

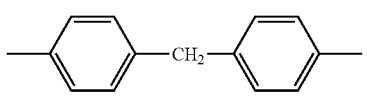

The group obtained by combination thereof includes, for example, xylylene group.

The alkylene group, the arylene group and the group by combination thereof may further have substituents, and the substituents include, for example, halogen atoms (e.g., fluorine, chlorine, bromine and iodine atoms), aryl, alkoxy (e.g., methoxy, ethoxy, 2-ethoxyethoxy), aryloxy (e.g., phenoxy), acyl (e.g., acetyl, propionyl), acyloxy (e.g., acetoxy, butyryloxy), alkoxycarbonyl (e.g., methoxycarnonyl, ethoxycarbonyl), and aryloxycarbonyl (e.g., phenoxycarbonyl).

In the above structural formulae (13) and (14), n represents an integer of 3 to 6, and the integer of 3, 4 or 6 is preferable in terms of raw material supply for synthesizing the polymerizable monomer.

In the above structural formulae (13) and (14), Z represents an n-valent (trivalent to hexavalent) linking group, and includes any of the groups shown below.

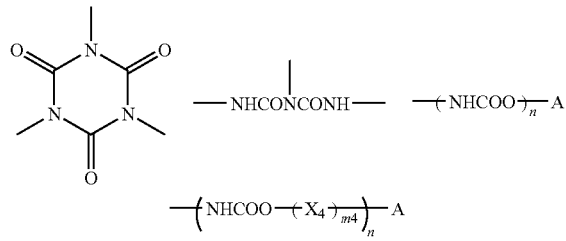

$X_4$ represents alkylene oxide, m4 represents an integer of 1 to 20, n represents an integer of 3 to 6, and A represents an n-valent (trivalent to hexavalent) organic group.

As the above A, an n-valent aliphatic group, an n-valent aromatic group, or groups obtained by combining these with the alkylene, arylene, alkenylene, alkynylene, carbonyl group, the oxygen atom, the sulfur atom, imino group, the substituted imino in which the hydrogen atom in the imino group has been substituted with the monovalent hydrocarbon group or the sulfonyl group are preferable. The n-valent aliphatic group, the n-valent aromatic group, or the groups obtained by combining alkylene, arylene or oxygen therewith are more preferable, and the n-valent aliphatic group and the group obtained by combining the alkylene or and the oxygen atom with the n-valent aliphatic group are particularly preferable.

The carbon atom number in the above A is, for example, preferably the integer of 1 to 100, more preferably 1 to 50 and particularly preferably 3 to 30.

The n-valent aliphatic group may have the branched structure or the cyclic structure.

The carbon atom number in the above aliphatic group is, for example, preferably the integer of 1 to 30, more preferably 1 to 20 and particularly preferably 3 to 10.

The carbon atom number in the above aromatic group is, for example, preferably the integer of 6 to 100, more preferably 6 to 50 and particularly preferably 6 to 30.

The n-valent aliphatic group or aromatic group may further have substituents. The substituents include, for example, hydroxyl, halogen atoms (e.g., fluorine, chlorine, bromine, iodine atoms), aryl groups, alkoxy groups (e.g., methoxy, ethoxy, 2-ethoxyethoxy), aryloxy groups (e.g., phenoxy), acyl groups (e.g., acetyl, propionyl), acyloxy groups (e.g., acetoxy, butyryloxy), alkoxycarbonyl groups (e.g., methoxycarnonyl, ethoxycarbonyl), and aryloxycarbonyl groups (e.g., phenoxycarbonyl).

The alkylene group may have the branched structure or the cyclic structure.

The carbon atom number in the above alkylene group is, for example, preferably the integer of 1 to 18 and more preferably 1 to 10.

The above arylene group may further be substituted with the hydrocarbon group.

The carbon atom number in the above arylene group is, for example, preferably the integer of 6 to 18 and more preferably 6 to 10.

The carbon atom number in the monovalent hydrocarbon group in the above substituted imino group is preferably the integer of 1 to 18 and more preferably 1 to 10.

The above A includes suitably, for example the groups shown below.

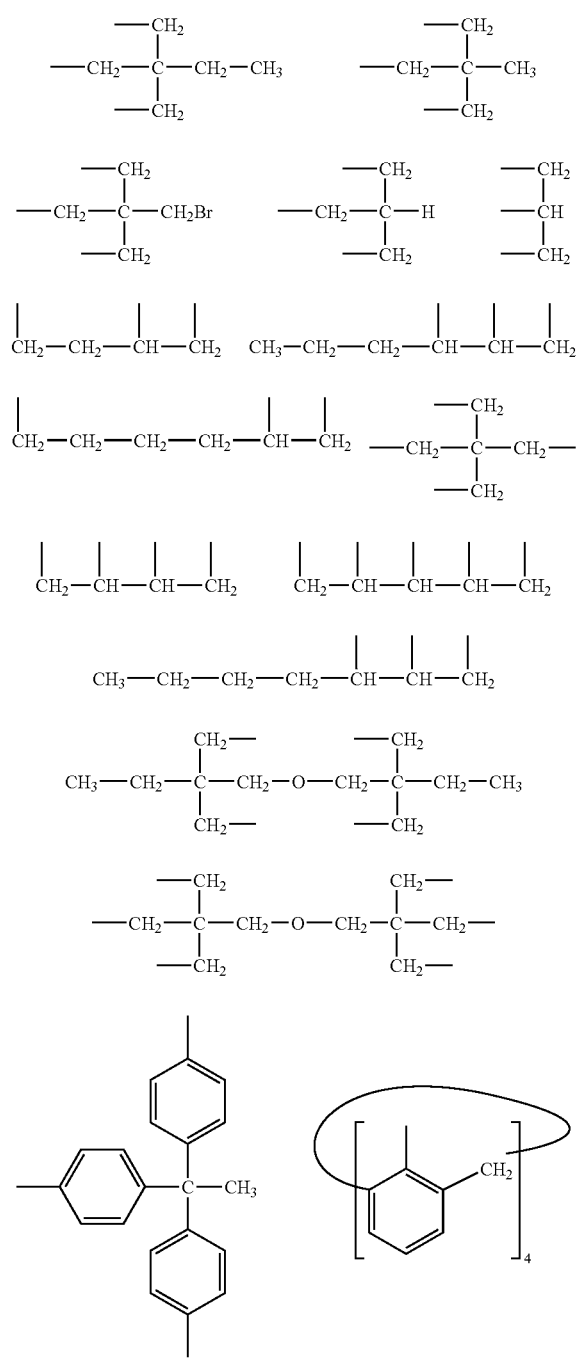

-continued
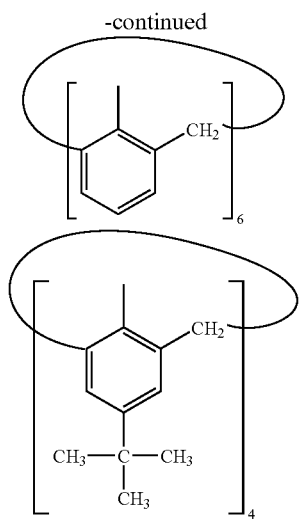
-continued
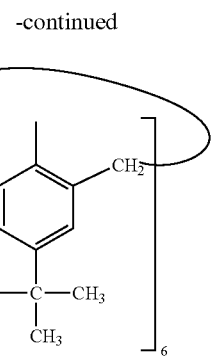
The compounds represented by the above structural formulae (13) and (14) include, for example, the compounds represented by the following structural formulae (15) to (35).
structural formula (15)
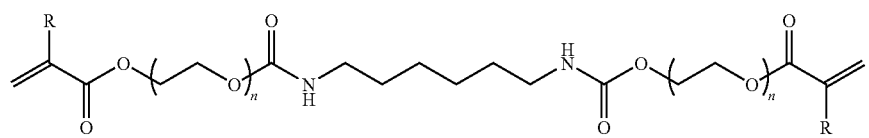
structural formula (16)
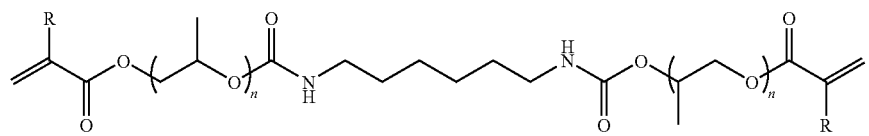
structural formula (17)
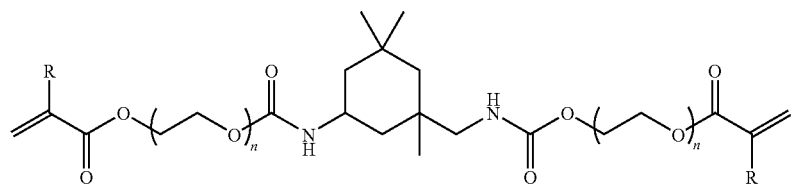
structural formula (18)
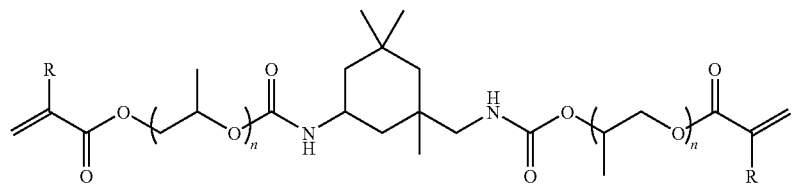
structural formula (19)
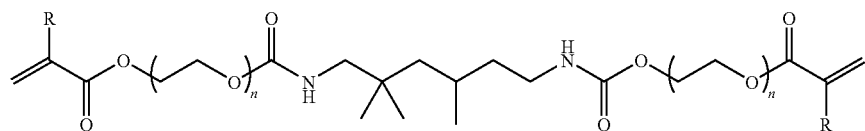
structural formula (20)
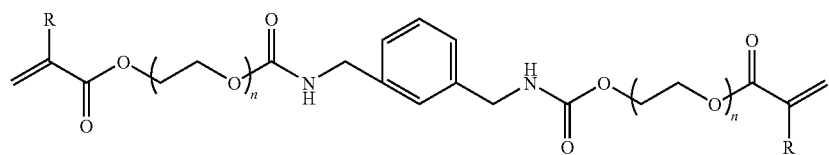

structural formula (21)
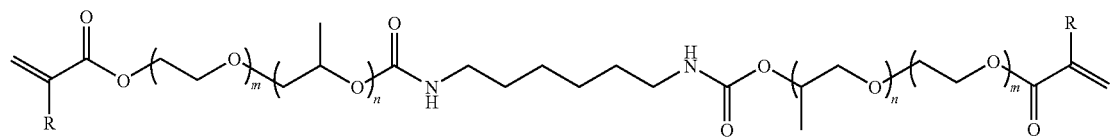
structural formula (22)
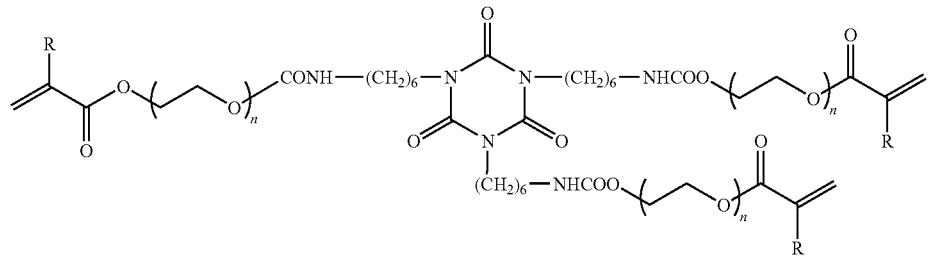
structural formula (23)
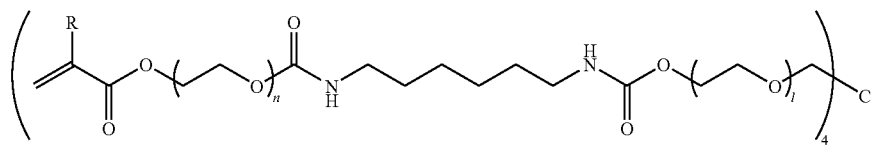
structural formula (24)
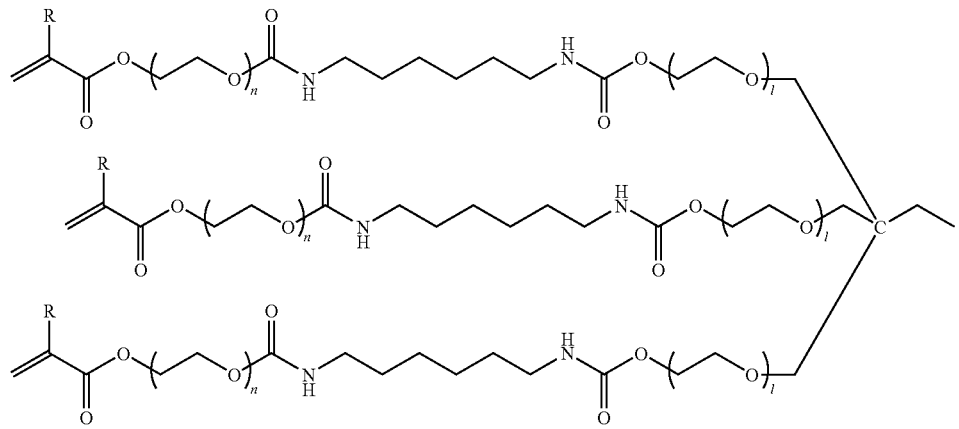
structural formula (25)
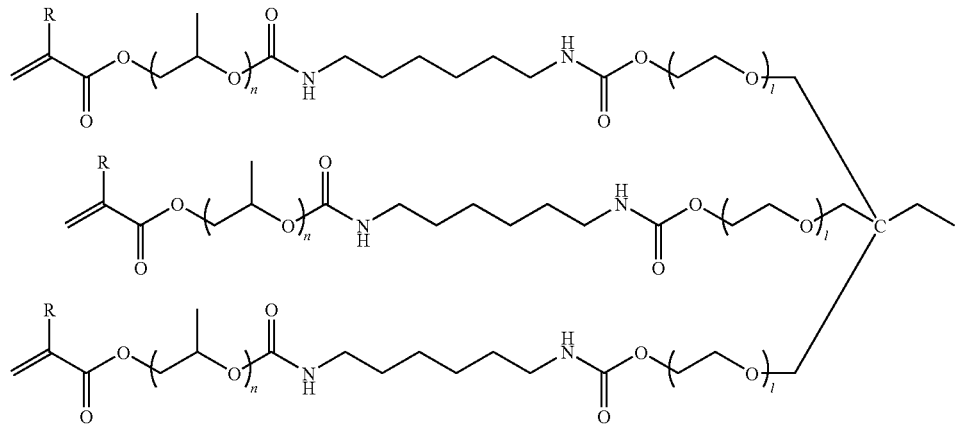

structural formula (26)
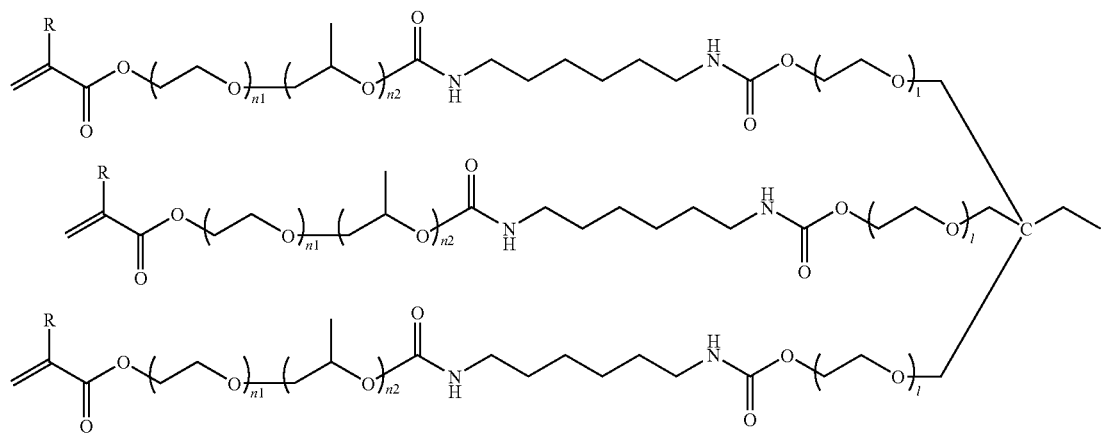
structural formula (27)
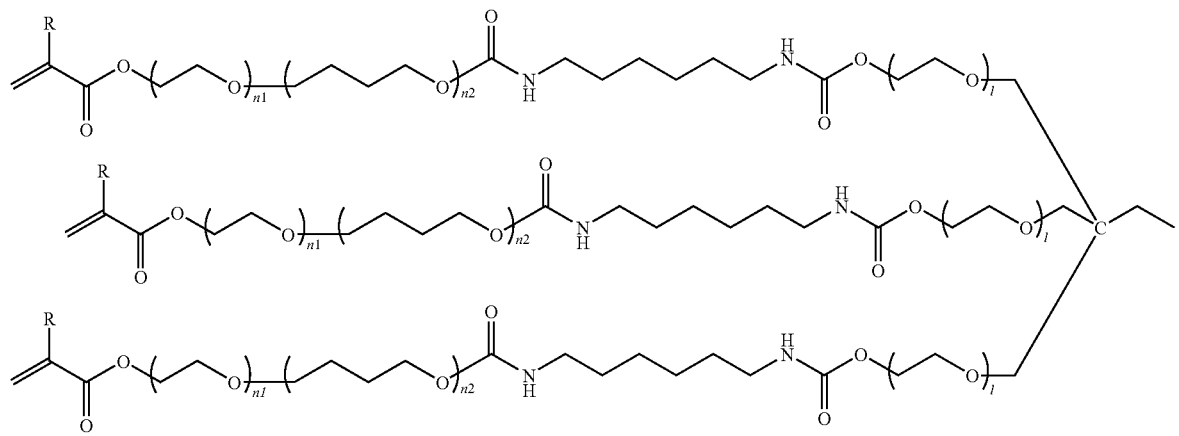
structural formula (28)
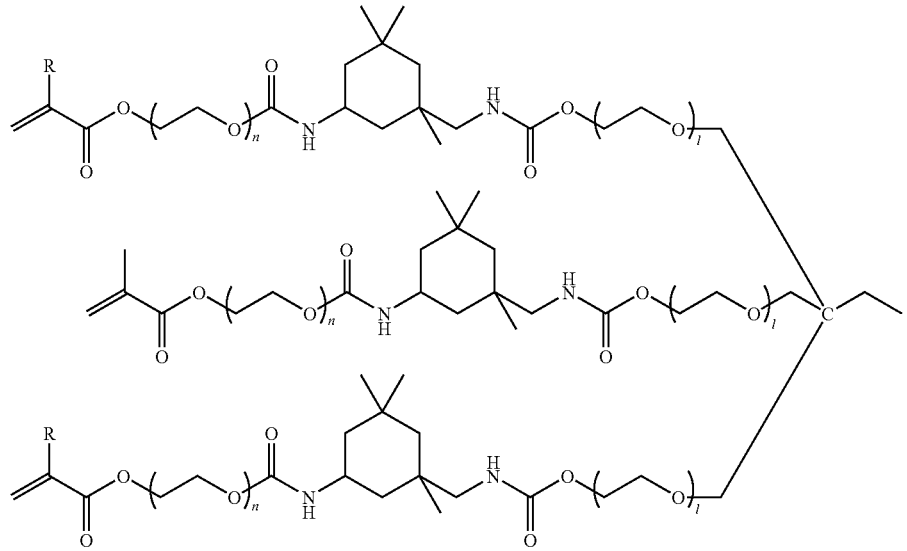

-continued
structural formula (29)
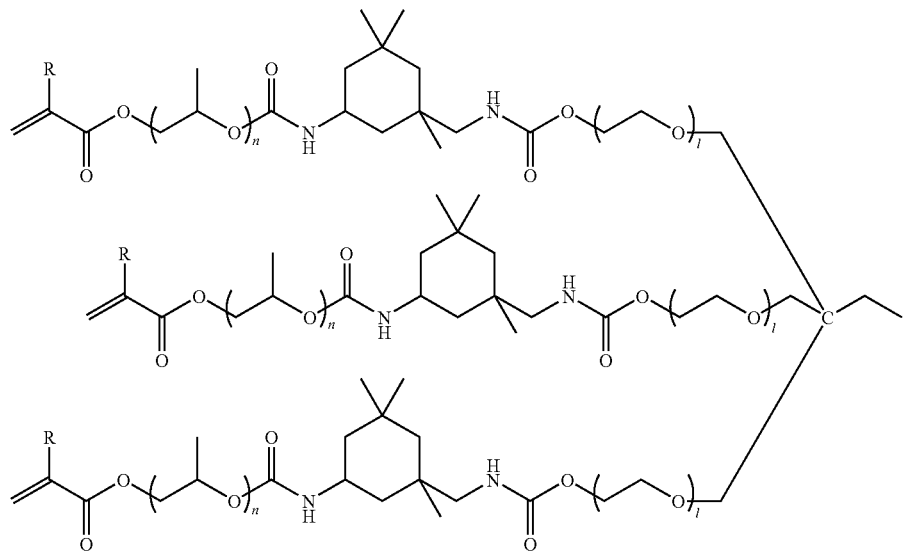
structural formula (30)
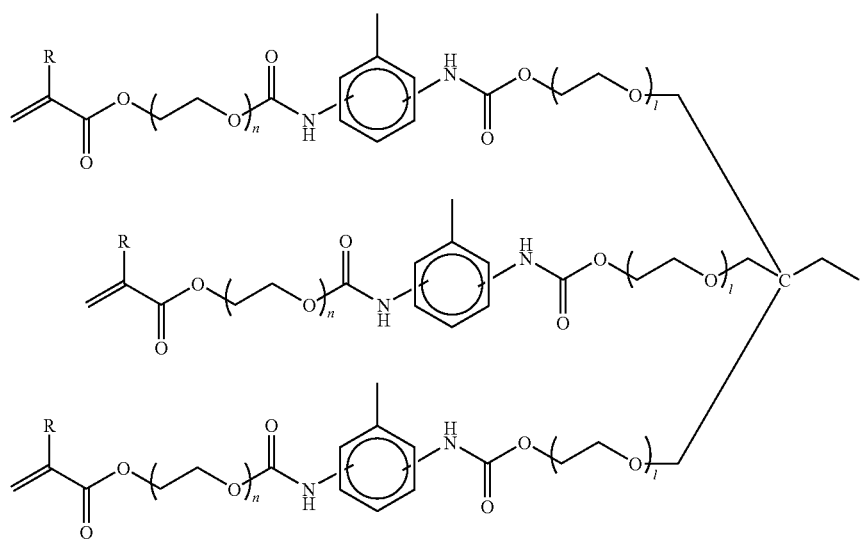
structural formula (31)
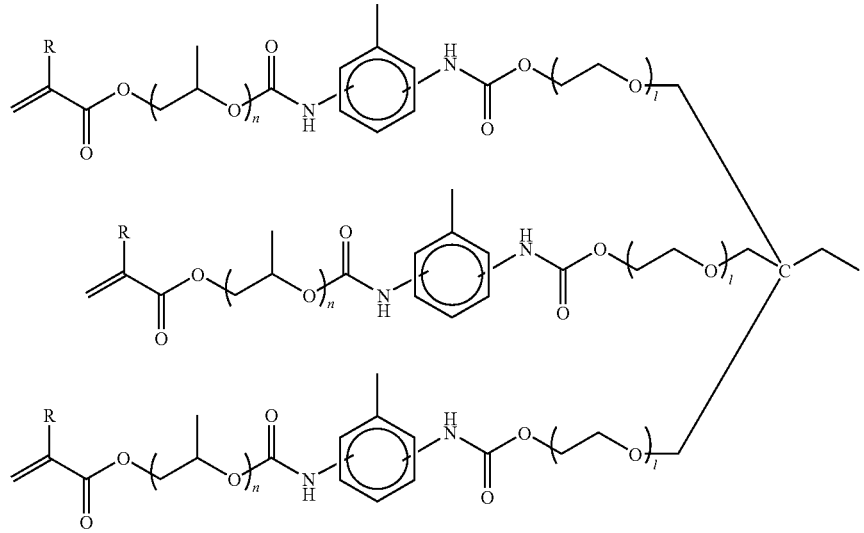

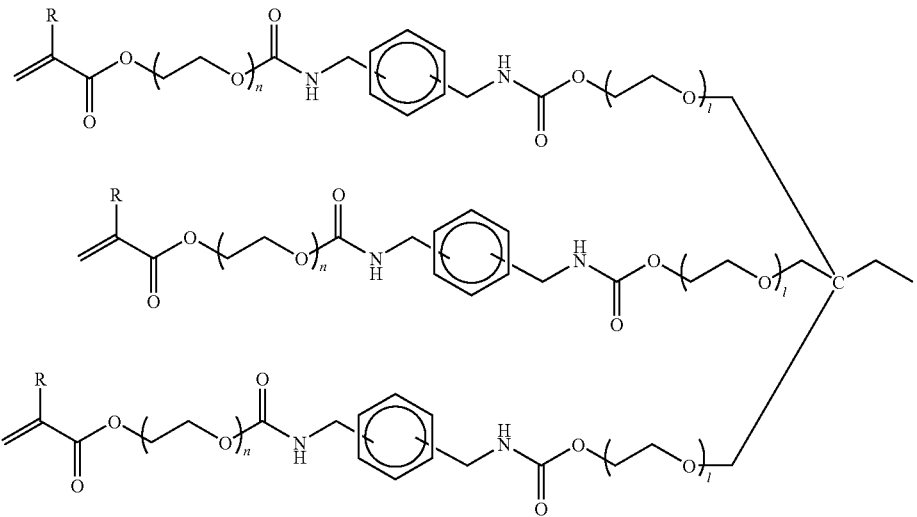
structural formula (32)
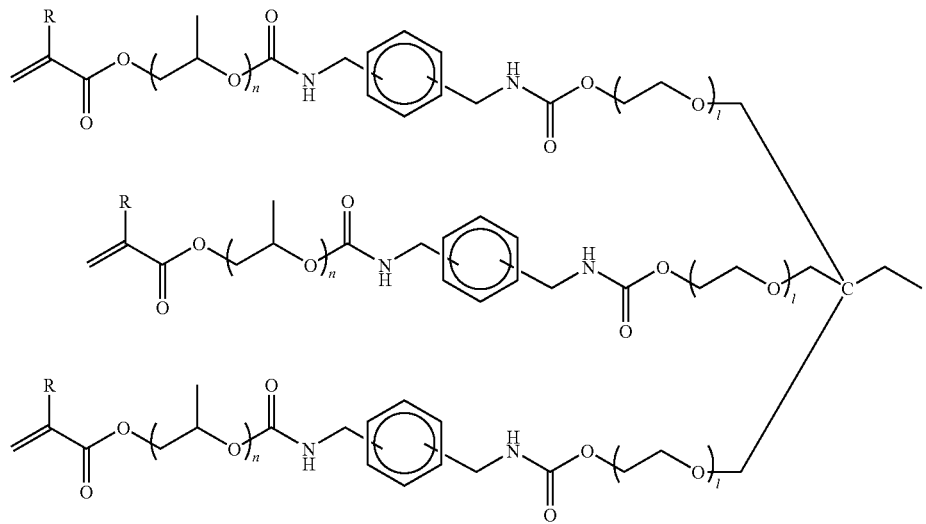
structural formula (33)
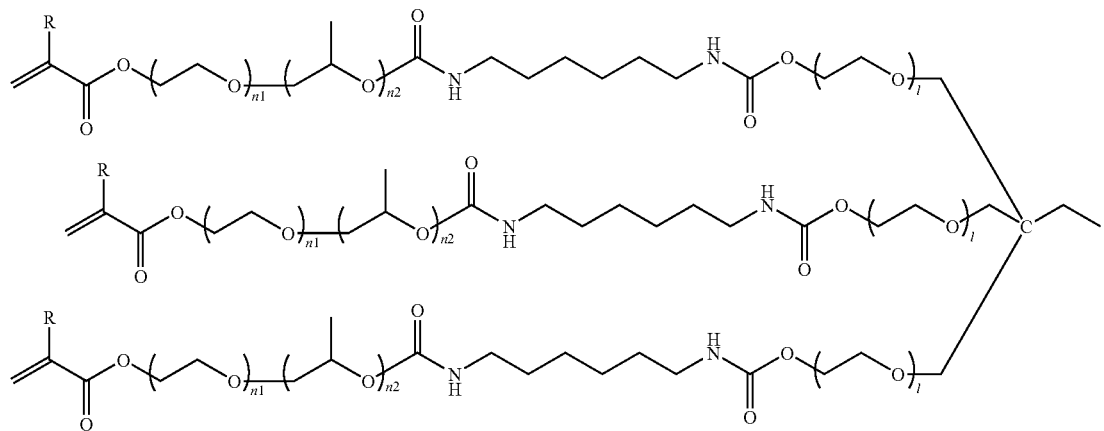
structural formula (34)

structural formula (35)

[chemical structure]

In the above structural formulae (15) to (35), n, n1, n2 and m mean 1 to 60, l means 1 to 20, and R represents a hydrogen atom or a methyl group.

—Monomer Having Aryl Group—

The monomer having the aryl group is not particularly limited as long as it has the aryl group, can be appropriately selected depending on the purpose, and includes, for example, esters or amides of at least any one of a polyvalent alcohol compound, a polyvalent amine compound and a polyvalent amino alcohol compound having the aryl group with unsaturated carboxylic acid.

The polyvalent alcohol compound, the polyvalent amine compound and the polyvalent amino alcohol compound having the aryl group include, for example, polystyrene oxide, xylylene diol, di-(β-hydroxyethoxy)benzene, 1,5-dihydroxy-1,2,3,4-tetrahydronaphthalene, 2,2-diphenyl-1,3-propanediol, hydroxybenzyl alcohol, hydroxyethyl resorcinol, 1-phenyl-1,2-ethanediol, 2,3,5,6-tetramethyl-p-xylene-α,α'-diol, 1,1,4,4-tetraphenyl-1,4-butanediol, 1,1,4,4-tetraphenyl-2-butene-1,4-diol, 1,1'-bi-2-naphthol, dihydroxynaphthalene, 1,1'-methylene-2-naphthol, 1,2,4-benzenetriol, biphenol, 2,2'-bis(4-hydroxyphenyl)butane, 1,1-bis(4-hydroxyphenyl)cyclohexane, bis(hydroxyphenyl)methane, catechol, 4-chlororesorcinol, hydroquinone, methyl hydroquinone, methylene-2,4,6-trihydroxybenzoate, fluoroglycinol, pyrogallol, resorcinol, α-(1-aminoethyl)-p-hydroxybenzyl alcohol and 3-amino-4-hydroxyphenylsulfone. In addition, compounds obtained by adding α, β-unsaturated carboxylic acid to a glycidyl compound such as xylylenebis (meth)acrylamide, novolak type epoxy resin and bisphenol A diglycidyl ether, ester compounds obtained from a vinyl monomer containing hydroxyl group in the molecule with phthalic acid or trimellitic acid, diallyl phthalate, triallyl trimellitate, diallyl benzenesulfonate, cation polymerizable divinyl ethers as polymerizable monomers (e.g., bisphenol A divinyl ether), epoxy compounds (e.g., novolak type epoxy resins, bisphenol A diglycidyl ether), vinyl esters (e.g., divinyl phthalate, divinyl terephthalate, divinylbenzene-1,3-disulfonate), styrene compounds (e.g., divinyl benzene, p-allylstyrene, p-isopropenestyrene) are also included. Among them, the compound represented by the following structural formula (36) is preferable.

structural formula (36)

[chemical structure: $R^4$ ... COO—(X_5)_{m5}—Ar_1—T—Ar_2—(X_6)_{m6}—OCO ... $R^5$]

In the above structural formula (36), $R^4$ and $R^5$ represents a hydrogen atoms or an alkyl groups.

In the above structural formula (36), $X_5$ and $X_6$ represent alkylene oxide groups, which may be used alone or in combination of two or more, and the alkylene oxide groups include suitably, for example, ethylene oxide, propylene oxide, butylene oxide, pentylene oxide, hexylene oxide groups and combinations (may be combined in random or block) thereof. Among them, ethylene oxide, propylene oxide, butylene oxide and the combinations thereof are preferable, and ethylene oxide and propylene oxide are more preferable.

In the above structural formula (36), m5 and m6 are preferably integers of 1 to 60, more preferably 2 to 30 and particularly preferably 4 to 15.

In the above structural formula (36), T represents a bivalent linking group, and includes, for example, methylene, ethylene, MeCMe, $CF_3CCF_3$, CO and $SO_2$.

In the above structural formula (36), $Ar^1$ and $Ar^2$ represent aryl groups which may have substituents, and include, for example, phenylene and naphthylene. The substituents include, for example, alkyl, aryl, aralkyl, halogen, alkoxy group or combinations thereof.

Specific examples of the monomer having the aryl group include 2,2-bis[4-(3-(meth)acryloxy-2-hydroxypropoxy)phenyl]propane, 2,2-bis[4-((meth)acryloxyethoxy)phenyl]propane, 2,2-bis[4-((meth)acryloxypolyethoxy)phenyl]propane where 2 to 20 ethoxy groups have been substituted with phenolic OH groups (e.g., 2,2-bis[4-((meth)acryloxydiethoxy)phenyl]propane, 2,2-bis[4-((meth)acryloxytetraethoxy)phenyl]propane, 2,2-bis[4-((meth)acryloxypentaethoxy)phenyl]propane, 2,2-bis[4-((meth)acryloxydecaethoxy)phenyl]propane, 2,2-bis[4-((meth)acryloxypentadecaethoxy)phenyl]propane), 2,2-bis[4-((meth)acryloxypropoxy)phenyl]propane, 2,2-bis[4-((meth)

acryloxypolypropoxy)phenyl]propane where 2 to 20 ethoxy groups have been substituted with phenolic OH groups (e.g., 2,2-bis[4-((meth)acryloxydipropoxy)phenyl]propane, 2,2-bis[4-((meth)acryloxytetrapropoxy)phenyl]propane, 2,2-bis [4-((meth)acryloxypentapropoxy)phenyl]propane, 2,2-bis [4-((meth)acryloxydecapropoxy)phenyl]propane, 2,2-bis[4-((meth)acryloxypentadecapropoxy)phenyl]propane), or compounds containing both a polyethylene oxide skeleton and a polypropylene oxide skeleton in the same molecule as a polyether moiety of these compounds (e.g., the compound described in WO01/98832, and BPE-200, BPE-500, BPE-1000 commercially available from Shin-Nakamura Chemical Co., Ltd.), or polymerizable compounds having a bisphenol skeleton and an urethane group. In these compounds, the moiety derived from the bisphenol A skeleton may be changed to the moiety from bisphenol F or bisphenol S.

The polymerizable compound having the bisphenol skeleton and the urethane group includes, for example, compounds (e.g., 2-isocyanate ethyl (meth)acrylate, α, α-dimethyl-vinyl benzyl isocyanate) having the isocyanate group and the polymerizable group in the compound having hydroxyl group at the end, obtained as an addition or polyaddition product of bisphenol with ethylene oxide or propylene oxide.

—Other Polymerizable Monomers—

In the photosensitive composition of the present invention, the polymerizable monomer other than the monomer having the urethane group and the monomer having the aryl group may be combined in the range in which the properties of the photosensitive compound are not deteriorated.

The polymerizable monomers other than the monomer having the urethane group and the monomer having the aromatic ring include, for example, esters of unsaturated carboxylic acid (e.g., acrylic acid, methacrylic acid, itaconic acid, crotonic acid, isocrotonic acid, maleic acid) with an aliphatic polyvalent alcohol compound, and amides of unsaturated carboxylic acid with a polyvalent amine compound.

The monomers of the ester of unsaturated carboxylic acid with the aliphatic polyvalent alcohol compound include, for example, ethylene glycol di(meth)acrylate, polyethylene glycol di(meth)acrylate having 2 to 18 ethylene groups (e.g., diethylene glycol di(meth)acrylate, triethylene glycol di(meth)acrylate, tetraethylene glycol di(meth)acrylate, nonaethylene glycol di(meth)acrylate, dodecaethylene glycol di(meth)acrylate, tetradecaethylene glycol di(meth)acrylate), propylene glycol di(meth)acrylate, polypropylene glycol di(meth)acrylate having 2 to 18 propylene groups (e.g., dipropylene glycol di(meth)acrylate, tripropylene glycol di(meth) acrylate, tetrapropylene glycol di(meth)acrylate, dodecapropylene glycol di(meth)acrylate), neopentyl glycol di(meth) acrylate), neopentyl glycol di(meth)acrylate) modified with ethylene oxide, neopentyl glycol di(meth)acrylate) modified with propylene oxide, trimethylol propane tri(meth)acrylate, trimethylol propane di(meth)acrylate, trimethylol propane tri ((meth)acryloyloxypropyl)ether, trimethylol ethane tri(meth) acrylate, 1,3-propanediol di(meth)acrylate, 1,3-butanediol di(meth)acrylate, 1,4-butanediol di(meth)acrylate, 1,6-hexanediol di(meth)acrylate, tetramethylene glycol di(meth) acrylate, 1,4-cyclohexanediol di(meth)acrylate, 1,2,4-butanetriol tri(meth)acrylate, 1,5-pentanediol (meth)acrylate, pentaerythritol di(meth)acrylate, pentaerythritol tri(meth) acrylate, pentaerythritol tetra(meth)acrylate, dipentaerythritol penta(meth)acrylate, dipentaerythritol hexa(meth)acrylate, sorbitol tri(meth)acrylate, sorbitol tetra(meth)acrylate, sorbitol penta(meth)acrylate, sorbitol hexa(meth)acrylate, dimethylol dicyclopentane di(meth)acrylate, tricyclodecane di(meth)acrylate, neopentyl glycol di(meth)acrylate, trimethylolpropane di(meth)acrylate modified with neopentyl glycol, di(meth)acrylate of alkylene glycol chain (e.g., the compound described in WO01/98832) having at least one ethylene glycol chain and one propylene glycol chain, tri (meth)acrylate ester of trimethylolpropane to which at least either ethylene oxide or propylene oxide has been added, polybutylene glycol di(meth)acrylate, glycerine di(meth) acrylate, glycerine tri(meth)acrylate, and xylenol di(meth) acrylate as (meth)acrylate esters.

Among the above (meth)acrylate esters, ethylene glycol di(meth)acrylate, polyethylene glycol di(meth)acrylate, propylene glycol di(meth)acrylate, polypropylene glycol di(meth)acrylate, di(meth)acrylate of alkylene glycol chain having at least one ethylene glycol chain and one propylene glycol chain, trimethylolpropane tri(meth)acrylate, pentaerythritol tri(meth)acrylate, pentaerythritol triacrylate, pentaerythritol di(meth)acrylate, dipentaerythritol penta(meth) acrylate, dipentaerythritol hexa(meth)acrylate, glycerine tri (meth)acrylate, diglycerine di(meth)acrylate, 1,3-propanediol di(meth)acrylate, 1,2,4-butanetriol tri(meth) acrylate, 1,4-cyclohexanediol di(meth)acrylate, 1,5-pentanediol (meth)acrylate, neopentyl glycol di(meth) acrylate, and tri(meth)acrylate ester of trimethylolpropane to which ethylene oxide has been added are preferable in terms of being easily available.

The ester (itaconate ester) of the itaconic acid with the aliphatic polyvalent alcohol compound includes, for example, ethylene glycol diitaconate, propylene glycol diitaconate, 1,3-butanediol diitaconate, 1,4-butanediol diitaconate, tetramethylene glycol diitaconate, pentaerythritol diitaconate and sorbitol tetraitaconate.

The ester (crotonate ester) of the crotonic acid with the aliphatic polyvalent alcohol compound includes, for example, ethylene glycol dicrotonate, tetramethylene glycol dicrotonate, pentaerythritol dicrotonate and sorbitol tetracrotonate.

The ester (isocrotonate ester) of the isocrotonic acid with the aliphatic polyvalent alcohol compound includes, for example, ethylene glycol diisocrotonate, pentaerythritol diisocrotonate and sorbitol tetraisocrotonate.

The ester (maleate ester) of the maleic acid with the aliphatic polyvalent alcohol compound includes, for example, ethylene glycol dimaleate, triethylene glycol dimaleate, pentaerythritol dimaleate, and sorbitol tetramaleate.

Amides derived from the polyvalent amine compound and the unsaturated carboxylic acid include, for example, methylene bis(meth)acrylamide, ethylene bis(meth)acrylamide, 1,6-hexamethylene bis(meth)acrylamide, octamethylene bis (meth)acrylamide, diethylenetriamine tris(meth)acrylamide and diethylenetriamine bis(meth)acrylamide.

In addition, the polymerizable monomers also include, for example, compounds obtained by adding α, β-unsaturated carboxylic acid to a glycidyl group-containing compound such as butanediol-1,4-diglycidyl ether, cyclohexane dimethanol glycidyl ether, ethylene glycol diglycidyl ether, diethylene glycol diglycidyl ether, dipropylene glycol diglycidyl ether, hexanediol diglycidyl ether, trimethylolpropane triglycidyl ether, pentaerythritol tetraglycidyl ether and glycerine triglycidyl ether, polyester acrylate and polyester (meth)acrylate oligomers as described in JP-A No. 48-64183, JP-B No. 49-43191 and JP-B No. 52-30490, polyfunctional acrylate and methacrylate such as epoxy acrylate obtained by reacting an epoxy compound (e.g., butanediol-1,4-diglycidyl ether, cyclohexane dimethanol glycidyl ether, diethylene glycol diglycidyl ether, dipropylene glycol diglycidyl ether, hexanediol diglycidyl ether, trimethylolpropane triglycidyl ether, pentaerythritol tetraglycidyl ether and glycerine triglycidyl ether) with (meth)acrylic acid, photocurable monomers and oligomers described in Journal of the Adhesion Society of Japan Vol. 20, No. 7:300-308, 1984, allyl esters (e.g., diallyl phthalate, diallyl adipate, diallyl malonate), diallyl amides (e.g., diallyl acetamide), cation polymerizable divinyl ethers (e.g., butanediol-1,4-divinyl ether, cyclohexane dimethanol glycidyl ether, ethylene glycol divinyl ether, diethylene glycol divinyl ether, dipropylene glycol divinyl ether, hexanediol divinyl ether, trimethylolpropane trivinyl ether, pentaerythritol tetravinyl ether and glycerine trivinyl ether), epoxy compounds (e.g., butanediol-1,4-diglycidyl ether, cyclohexane dimethanol glycidyl ether, ethylene glycol diglycidyl ether, diethylene glycol diglycidyl ether, dipropylene glycol diglycidyl ether, hexanediol diglycidyl ether, trimethylolpropane triglycidyl ether, pentaerythritol tetraglycidyl ether and glycerine triglycidyl ether), oxetanes (e.g., 1,4-bis[(3-ethyl-3-oxetanylmethoxy)methyl]benzene), and compounds having two or more different ethylenic unsaturated double bonds, such as epoxy compounds, oxetanes (e.g., the compound described in WO01/22165), N-hydroxyethyl-β-(methacrylamide)ethyl acrylate, N,N-bis(β-methacryloyoxyethyl)acrylamide and allyl methacrylate.

The vinyl esters include, for example, divinyl succinate and divinyl adipate.

These polyfunctional monomers and oligomers may be used alone or in combination of two or more.

The polymerizable monomer may be combined with the polymerizable compound (monofunctional monomer) having one polymerizable group in the molecule if necessary.

The monofunctional monomer includes, for example, the compounds exemplified as the raw material of the binder, monofunctional monomers such as two basic mono((meth)acryloyloxyalkyl ester)mono(halohydroxyalkyl ester) described in JP-A No. 06-236031 (e.g., γ-chloro-β-hydroxypropyl-β'-methacryloyloxyethyl-o-phthalate), and the compounds described in U.S. Pat. No. 2,744,643, WO00/52529 and U.S. Pat. No. 2,548,016.

The content of the polymerizable compound in the photosensitive composition is, for example, preferably 5% by mass to 90% by mass, more preferably 15% by mass to 60% by mass and particularly preferably 20% by mass to 50% by mass.

When the content is 5% by mass, the strength of the tent membrane is sometimes reduced, and when it exceeds 90% by mass, the edge fusion (soaking out trouble from roll edge) in storage is sometimes deteriorated.

The content of the polyfunctional monomer having two or more polymerizable groups in the polymerizable compound is preferably 5% by mass to 100% by mass, more preferably 20% by mass to 100% by mass, and particularly preferably 40% by mass to 100% by mass.

—Photopolymerization Initiator—

As the photopolymerization initiator, the titanocene based compound of the present invention is used. The titanocene based compound of the present invention is as described already.

The content of the photopolymerization initiator in the photosensitive composition is preferably 0.1% by mass to 30% by mass, more preferably 0.5% by mass to 20% by mass, and particularly preferably 0.5% by mass to 15% by mass.

The other ingredients include, for example, sensitizers, thermal polymerization inhibitors, plasticizers, color forming agents and coloring agents. Additionally, adhesion accelerators to a substrate surface and other aids (e.g., pigments, conductive particles, fillers, anti-foaming agents, flame retardants, leveling agents, peeling accelerators, antioxidants, perfumes, thermal crosslinkers, surface tension adjusters, chain transfer agents) may be combined. By appropriately containing these ingredients, it is possible to control natures such as stability, photographic property, printout property and membrane physical property of the photosensitive composition.

—Sensitizer—

The sensitizer can be appropriately selected by visible light, ultraviolet light/visible light laser as a light irradiation procedure described later.

The sensitizer can generate a useful group such as radical and acid by making an excitation state with active energy ray and interacting (e.g., energy transfer, electron transfer) with the other substance (e.g., radical generator, acid generator).

The sensitizer is not particularly limited, can be appropriately selected from the sensitizers known publicly, and includes, for example, publicly known polynuclear aromatic chemicals (e.g., pyrene, perylene, triphenylene), xanthenes (e.g., fluorescein, eosin, erythrosine, rhodamine B, rose Bengal), cyanines (e.g., indocarbocyanine, thiacarbocyanine, oxacarbocyanine), merocyanines (merocyanine, carbomerocyanine), thiazines (e.g., thionine, methylene blue, toluidine blue), acridines (e.g., acridine orange, chloroflavin, acriflavin), anthraquinones (e.g., anthraquinone), squariums (e.g., squarium), acridones (e.g., acridone, chloroacridone, N-methylacridone, N-butylacridone, N-butyl-chloroacridone), coumarins (e.g., benzofluoyl-7-diethylaminocoumarin, 3-(2-benzofluoyl)-7-(1-pyrolizinyl)coumarin, 3-benzoyl-7-diethylaminocoumarin, 3-(2-methoxybenzoyl)-7-diethylaminocoumarin, 3-(4-dimethylaminobenzoyl)-7-diethylaminocoumarin, 3,3'-carbonylbis(5,7-n-propoxycoumarin), 3-(2-fluoyl)-7-diethylaminocoumarin, 3-(4-diethylaminocinnamoyl)-7-diethylaminocoumarin, 7-methoxy-3-(3-pyridinylcarbonyl)coumarin, and 3-benzoyl-5,7-dipropoxycoumarin. Additionally, coumarin compounds described in JP-A No. 05-19475, JP-A No. 07-271028, JP-A No. 2002-363206, JP-A No. 2002-363207, JP-A No. 2002-363208 and JP-A No. 2002-363209 are included.

The content of the sensitizer is preferably 0.05% by mass to 30% by mass, more preferably 0.1% by mass to 20% by mass and particularly preferably 0.2% by mass to 10% by mass relative to all ingredients in the photosensitive composition.

When the content is less than 0.05% by mass, sensitivity to the active energy ray is reduced, an exposure process takes a long time and productivity is reduced. When it exceeds 30% by mass, the sensitizer is sometimes precipitated from a photosensitive layer of a photosensitive transfer sheet described later in storage.

—Thermal Polymerization Inhibitor—

The thermal polymerization inhibitor may be added in order to prevent thermal polymerization or the polymerization with time of the polymerizable compound.

The thermal polymerization inhibitor includes, for example, 4-methoxyphenol, hydroquinone, alkyl or aryl-substituted hydroquinone, t-butyl catechol, pyrogal, 2-hydroxybenzophenone, 4-methoxy-2-hydroxybenzophenone, cuprous chloride, phenothiazine, chloranil, naphthylamine, β-naphthol, 2,6-t-butyl-4-cresol, 2,2'-methylenebis(4-methyl-6-butylphenol), pyridine, nitrobenzene, dinitrobenzene, picric acid, 4-toluidine, methylene blue, reactant of copper and organic chelator, methyl salicylate, and phenothiazine, nitroso compounds, chelated products of the nitroso compound and A1.

The content of the thermal polymerization inhibitor is preferably 0.001% by mass to 5% by mass, more preferably 0.005% by mass to 2% by mass, and particularly preferably 0.01% by mass to 1% by mass relative to the polymerizable compound.

When the content is less than 0.001% by mass, the storage stability is sometimes reduced, and when it exceeds 5% by mass, the sensitivity to the active energy ray is sometimes reduced.

—Plasticizer—

The plasticizer may be added in order to control the membrane physical property (plasticity) of the photosensitive layer when this photosensitive layer is formed from the photosensitive composition of the present invention.

The plasticizer includes, for example, phthalate esters such as dimethyl phthalate, dibutyl phthalate, diisobutyl phthalate, diheptyl phthalate, dioctyl phthalate, dicyclohexyl phthalate, ditridecyl phthalate, octylcapril phthalate; glycol esters such as triethylene glycol diacetate, tetraethylene glycol diacetate, dimethyl glycol phthalate, ethylphthalylethyl glycolate, methylphthalylethyl glycolate, butylphthalylbutyl glycolate and triethylene glycol caprylate ester; phosphate esters such as tricrezyl phosphate and triphenyl phosphate; amides such as 4-toluene sulfonamide, benzene sulfonamide, N-n-butylbenzene sulfonamide and N-n-butyl acetamide; aliphatic dibasic acid esters such as diisobutyl adipate, dioctyl adipate, dimethyl sebacate, dibutyl sebacate, dioctyl sebacate, dioctyl azelate and dibutyl maleate; triethyl citrate, tributyl citrate, glycerine triacetyl ester, butyl laurate, 4,5-diepoxycyclohexane-1, dioctyl 2-carboxylate, and glycols such as polyethylene glycol and polypropylene glycol.

The content of the plasticizer is preferably 0.1% by mass to 50% by mass, more preferably 0.5% by mass to 40% by mass, and particularly preferably 1% by mass to 30% by mass relative to all ingredients in the photosensitive composition.

—Color Forming Agent—

The color forming agent may be added in order to impart a visible image to the photosensitive layer after exposure (printout function).

The color forming agent includes, for example, aminotriarylmethanes such as tris(4-dimethylaminophenyl)methane (leucocrystal violet), tris(4-diethylaminophenyl)methane, tris(4-dimethylamino-2-methyphenyl)methane, tris(4-diethylamino-2-methyphenyl)methane, bis(4-dibutylaminophenyl)-[4-(2-cyanoethyl)methylaminophenyl]methane, bis(4-dimethylaminophenyl)-2-quinolylmethane and tris(4-dipropylaminophenyl)methane; aminoxanthines such as 3,6-bis(dimethylamino)-9-phenylxanthine, 3-amino-6-dimethylamino-2-methyl-9-(2-chlorophenyl)xanthine; aminothioxanthenes such as 3,6-bis(diethylamino)-9-(2-ethoxycarbonylphenyl)thioxanthene and 3,6-bis(dimethylamino)thioxanthene; amino-9,10-dihydroacridines such as 3,6-bis(diethylamino)-9,10-dihydro-9-phenylacridine, 3,6-bis(benzylamino)-9,10-dihydro-9-methylacridine; amino phenoxazines such as 3,7-bis(diethylamino)phenoxazine; amino phenothiazines such as 3,7-bis (ethylamino)phenothiazine; amino dihydrophenazines such as 3,7-bis(diethylamino)-5-hexyl-5,10-dihydrophenazine; amino phenyl methanes such as bis(4-dimethylaminophenyl)anilinomethane; amino hydrocinnamates such as 4-amino-4-dimethylaminodiphenylamine and 4-amino-α, β-dicyanohydrocinnamate methyl ester; hydrazines such as 1-(2-naphthyl)-2-phenylhydrazine; amino-2,3-dihydroanthraquinones such as 1,4-bis(ethylamino)-2,3-dihydroanthraquinone; phenethyl anilines such as N,N-diethyl-4-phenethyl aniline; acyl derivatives of leuco dye containing basic NH, such as 10-acetyl-3,7-bis(dimethylamino)phenothiazine; leuco like compounds not having hydrogen capable of being oxidized but capable of being oxidized to a color forming compound, such as tris(4-diethylamino-2-tolyl)ethoxycarbonylmethane; leuco indigoid dyes; organic amines capable of being oxidized to a color forming type as described in U.S. Pat. Nos. 3,042,515 and 3,042,517 (e.g., 4,4'-ethylenediamine, diphenylamine, N,N-dimethyl aniline, 4,4'-methylenediamine triphenylamine, N-vinyl carbazole). Among them, the triarylmethane based compounds such as leuco crystal violet are preferable.

Furthermore, it is generally known that the color forming agent is combined with a halogen compound for the purpose of forming the color of the leuco body.

The halogen compounds include, for example, halogenated hydrocarbon (e.g., carbon tetrabromide, iodoform, ethylene bromide, methylene bromide, amyl bromide, isoamyl bromide, amyl iodide, isobutylene bromide, butyl iodide, diphenylmethyl bromide, hexachloroethane, 1,2-dibromoethane, 1,1,2,2-tetrabromoethane, 1,2-dibromo-1,1,2-trichloroethane, 1,2,3-tribromopropane, 1-bromo-4-chorobutane, 1,2,3,4-tetrabromobutane, tetrachloropropene, hexachlorooentadiene, dibromocyclohexane, 1,1,1-trochloro-2,2-bis(4-chloroohenyl)ethane); halogenated alcohol compounds (e.g., 2,2,2-trichoroethanol, tribromoethanol, 1,3-dichloro-2-propanol, 1,1,1-trichloro-2-propanol, di(iodohexamethylene)amino isopropanol, tribromo-t-butyl alcohol, 2,2,3-trichlorobutane-1,4-dial); halogenated carbonyl compounds (e.g., 1,1-dichloroacetone, 1,3-dichloroacetone, hexachloroacetone, hexabromoacetone, 1,1,3,3-tetrachloroacetone, 1,1,1-trichloroacetone, 3,4-dibromo2-butanone, 1,4-dichloro-2-butanone-dibromocyclohexanone); halogenated ether compounds (e.g., 2-bromoethylmethyl ether, 2-bromoethylethyl ether, di(2-bromoethyl) ether, 1,2-dichloroethyl ether); halogenated ester compounds (e.g., bromoethyl acetate, ethyl tricHoroacetate, trichloroethyl trichloroacetate, homopolymers and copolymers of 2,3-dibromopropyl acrylate, trichloroethyl dibromopropionate, ethyl α, β-dichloroacrylate); halogenated amide compounds (e.g., chloroacetamide, bromoacetamide, dichloroacetamide, trichloroacetamide, tribromoacetamide, trichloroethyltrichloroacetamide, 2-bromoisopropyonamide, 2,2,2-trichloropropyonamide, N-chlorosuccineimide, N-bromosuccineimide); compounds having sulfur or phosphorus (e.g., tribromomethylphenylsulfone, 4-nitrophenyltribromomethylsulfone, 4-chlorophenyltrobromomethylsulfone, tris (2,6-dibromopropyl)phosphate), and 2,4-bis(trichloromethyl) 6-phenyltriazole. In the organic halogen compounds, the halogen compound having two or more halogen atoms bound to the same carbon atom is preferable, and the halogen compound having three halogen atoms bound to one carbon atom is more preferable. The organic halogen compound may be used alone or in combination of two or more. Among them, tribromomethylphenylsulfone and 2,4-bis(trichloromethyl)-6-phenyltriazole are preferable.

The content of the color forming agent is preferably 0.01% by mass to 20% by mass, more preferably 0.05% by mass to 10% by mass and particularly preferably 0.1% by mass to 5% by mass relative to the all ingredients in the photosensitive composition. The content of the halogen compound is preferably 0.001% by mass to 5% by mass and more preferably 0.005% by mass to 1% by mass relative to the all ingredients of the photosensitive composition.

—Dyes—

The dye can be used in the photosensitive composition for the purpose of coloring the photosensitive composition for enhancing handling property, or imparting the storage stability.

The dyes can include brilliant green (e.g. sulfate salts thereof), eosin, ethyl violet, erythrosine B, methyl green, crystal violet, basic fuchsine, phenolphthalein, 1,3-diphenyltriazine, alizarin red S, thymolphthalein, methyl violet 2B, quinaldine red, rose Bengal, metanyl yellow, thymolsulfophthalein, xylenol blue, methyl orange, orange IV, diphenylthiocarbazone, 2,7-dichlorofluorescein, paramethyl red, congo red, benzopurpurin 4B, α naphthyl red, Nile blue A, phenacetarine, methyl violet, malachite green, parafuchsine, oil blue #603 (supplied from Orient Chemical Industries Ltd.), rhodamine B, rhodamine 6G, and Victoria pure blue BOH. Among them, cation dyes (e.g., malachite green oxalate salts, malachite green sulfate salts) are preferable. Counteranion of the cation dye could be residues of organic or inorganic acids. For example, the residues (anions) of bromic acid, iodic acid, sulfuric acid, phosphoric acid, oxalic acid, methanesulfonic acid and toluenesulfonic acid are included.

The content of the dye is preferably 0.001% by mass to 10% by mass, more preferably 0.01% by mass to 5% by mass and particularly preferably 0.1% by mass to 2% by mass relative to the all ingredients in the photosensitive composition.

—Adhesion Accelerator—

A publicly known, so-called adhesion accelerator can be used in order to enhance the adhesion to the substrate when the photosensitive transfer sheet described later is formed.

The adhesion accelerator includes suitably, for example, the adhesion accelerators described in JP-A No. 05-11439, JP-A No. 05-341532 and JP-A No. 06-43638.

Specifically, benzimidazole, benzoxazole, benzothiazole, 2-mercaptobenzimidazole, 2-mercaptobenzoxazole, 2-mercaptobenzothiazole, 3-morphlinomethyl-1-phenyl-triazole-2-thione, 3-morphlinomethyl-5-phenyl-oxadiazole-2-thione, 5-amino-3-morpholinomethyl-thiadiazole-2-thione and 2-mercapto-5-methylthio-thiadiazole, triazole, tetrazole, benzotriazole, carboxybenzotriazole, amino group-containing benzotriazole, and silane coupling agents are included.

The content of the adhesion accelerator is preferably 0.001% by mass to 20% by mass, more preferably 0.01% by mass to 10% by mass and particularly preferably 0.1% by mass to 5% by mass relative to the all ingredients in the photosensitive composition.

The photosensitive composition may contain an organic sulfur compound, peroxide, a redox based compound, an azo or diazo compound, a photoreduction dye, an organic halogen compound and the like as described in, for example, "Light Sensitive Systems" Section 5 written by J. Kosar.

The organic sulfur compound includes, for example, d-n-butyldisulfide, dibenzyldisulfide, 2-mercaptobenzthiazole, 2-mercaptobenzoxazole, thiophenol, ethyltrichloromethane-sulfenate, and 2-mercaptobenzimidazole.

The peroxide includes, for example, di-t-butyl peroxide, benzoyl peroxide and methyl ethyl ketone peroxide.

The redox compound is composed of the combination of the peroxide and a reducing agent, and can include ferrous ion and peroxide ion, and ferric ion and peroxide.

The azo or diazo compound includes, for example, α,α'-azobis-iso-butyronitrile, 2-azobis-2-methylbutyronitrile and diazoniums of 4-aminodiphenylamine.

The photoreduction dye includes, for example, rose Bengal, erythrosine, eosin, acriflavin, riboflavin and thionine.

—Surfactant—

The surfactant known publicly can be added in order to improve sheet unevenness generated when the photosensitive transfer film of the present invention described later is produced.

The surfactant can be appropriately selected from anionic surfactants, cationic surfactants, nonionic surfactants, ampholytic surfactants, and fluorine-containing surfactants.

The content of the surfactant is preferably 0.001% by mass to 10% by mass relative to the solid content in the photosensitive composition.

When the content is less than 0.001% by mass, the effect of sheet improvement is not sometimes obtained. When it exceeds 10% by mass, the adhesion is sometimes reduced.

As the surfactants, in addition to the above surfactants, as the fluorine based surfactants, polymer surfactants having acrylate or methacrylate having a fluoro aliphatic group comprising 40% by mass or more fluorine atoms with 3 to 20 carbon atoms, where hydrogen atoms bound to at least three carbon atoms counted from a non-bound end have been substituted with fluorine atoms, as a copolymer component are included suitably.

The photosensitive composition of the present invention can enhance the sensitivity by comprising the titanocene based compound of the present invention as the photopolymerization initiator, therefore, can be used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs), and pattern forming materials, and can be particularly used suitably for the photosensitive transfer sheet of the present invention.

(Photosensitive Transfer Sheet)

The photosensitive transfer sheet of the present invention has at least a support and a photosensitive layer, and preferably has a protection film.

A form of the photosensitive transfer sheet is not particularly limited, can be appropriately selected depending on the purpose, and includes, for example a form having the photosensitive layer and the protection film in this order on the support. The photosensitive layer may be a monolayer or a multilayer.

—Support—

The support is not particularly limited, can be appropriately selected depending on the purpose, and those capable of peeling the photosensitive layer and having good light permeability are preferable, and those further having good surface smoothness are more preferable.

Materials of the support are preferably synthetic resins and transparent, and include, for example, plastic films of polyethylene terephthalate, polyethylene naphthalate, polypropylene, polyethylene, cellulose triacetate, cellulose diacetate, poly(meth)acrylate alkyl ester, poly(meth)acrylate ester copolymer, polyvinyl chloride, polyvinyl alcohol, polycarbonate, polystyrene, cellophane, polyvinylidene chloride copolymer, polyamide, polyimide, vinyl chloride/vinyl acetate copolymer, polytetrafluoroethylene, polytrifluoroethylene, cellulose based film and nylon film. Among them, polyethylene terephthalate is particularly preferable. These may be used alone or in combination of two or more.

As the support, it is also possible to use the supports described, for example, in JP-A No. 04-208940, JP-A No. 05-80503, JP-A No. 05-173320 and JP-A No. 05-72724.

A thickness of the support is not particularly limited, can be appropriately selected depending on the purpose, and is preferably 4 μm to 300 μm and more preferably 5 μm to 175 μm.

A shape of the support is not particularly limited, can be appropriately selected depending on the purpose, and for example, it is preferable to be rolled up to a cylindrical core and stored in a lengthy roll shape.

A length of the lengthy photosensitive transfer sheet is not particularly limited, and can be appropriately selected from the range of 10 m to 20,000 m. For easy-to-use, a slit processing may be given to make a lengthy body a roll in the range of 100 m to 1,000 m. In this case, it is preferable to be rolled up so that the support is an outmost side. The photosensitive transfer sheet in a roll shape may be slit into a sheet shape. In the storage, it is preferable to dispose a separator (particularly, moisture proof, with drying agent), and use the material having low moisture permeability for package in terms of protection of an edge and prevention of edge fusion.

—Photosensitive Layer—

The photosensitive layer is formed from the photosensitive composition of the present invention. A site at which the photosensitive layer is provided in the photosensitive transfer sheet is not particularly limited, can be appropriately selected depending on the purpose, and the photosensitive layer is typically laminated on the support.

The thickness of the photosensitive layer is not particularly limited, can be appropriately selected depending on the purpose, and, for example, is preferably 1 µm to 100 µm and more preferably 5 µm to 70 µm.

—Protection Film—

The protection film has the function to prevent stain and damage of the photosensitive layer and protect the photosensitive layer.

A site at which the protection film is provided in the photosensitive transfer sheet is not particularly limited, can be appropriately selected depending on the purpose, and the protection film is typically provided on the photosensitive layer.

The protection film includes, for example those used for the support, silicone papers, papers laminated with polyethylene or polypropylene, polyolefin sheets or polytetrafluoroethylene sheets. Among them, polyethylene film and polypropylene films are preferable.

The thickness of the protection film is not particularly limited, can be appropriately selected depending on the purpose, and, for example is preferably 5 µm to 100 µm and more preferably 8 µm to 30 µm.

When the protection film is used, it is preferable that an adhesive force A between the photosensitive layer and the support and an adhesive force B between the photosensitive layer and the protection film have the relation of the adhesive force A> the adhesive force B.

The combination of the support and the protection film (support/protection film) includes, for example, polyethylene terephthalate/polypropylene, polyethylene terephthalate/polyethylene, polyvinyl chloride-cellophane, polyimide/polypropylene and polyethylene terephthalate/polyethylene terephthalate. By giving a surface treatment to at least either the support or the protection film, it is possible to satisfy the relation of such adhesive forces. The surface treatment of the support may be given to enhance the adhesive force to the photosensitive layer, and can include, for example, application of a primer layer, corona electric discharge, flame treatment, ultraviolet irradiation, highly frequent wave irradiation, glow discharge, active plasma irradiation and laser light irradiation.

A static friction coefficient between the support and the protection film is preferably 0.3 to 1.4 and more preferably 0.5 to 1.2.

When the static friction coefficient is less than 0.3, because of excessive sliding, rolling shift sometimes occurs when rolled up. When it exceeds 1.4, it becomes sometimes difficult to be rolled up well.

The surface treatment may be given to the protection film in order to control an adhesiveness between the protection film and the photosensitive layer. In the surface treatment, on the surface of the protection film, the primer layer composed of a polymer such as polyorganosiloxane, fluorinated polyolefin, polyfluoroethylene and polyvinyl alcohol is formed. The primer layer can be formed by applying a coating solution of the polymer on the surface of the protection film and subsequently drying at 30° C. to 150° C. (particularly 50° C. to 120° C.) for one minute to 30 minutes.

—Method for Producing Photosensitive Transfer Sheet—

The photosensitive transfer sheet can be produced, for example, as follows.

First, a photosensitive resin composition solution for the photosensitive transfer sheet is prepared by dissolving materials contained in the photosensitive composition in water or a solvent to emulsify or disperse.

The solvent is not particularly limited, can be appropriately selected depending on the purpose, and includes, for example, alcohols such as methanol, ethanol, n-propanol, isopropanol, n-butanol, sec-butanol and n-hexanol; ketones such as acetone, methyl ethyl ketone, methyl isobutyl ketone, cyclohexane and diisobutyl ketone; esters such as ethyl acetate, butyl acetate, n-amyl acetate, methyl sulfate, ethyl propionate, dimethyl phthalate, ethyl benzoate and methoxypropyl acetate; aromatic hydrocarbons such as toluene, xylene, benzene and ethyl benzene; halogenated hydrocarbon such as carbon tetrachloride, trichloroethylene, chloroform, 1,1,1-trichloroethane, methylene chloride and monochlorobenzene; ethers such as tetrahydrofuran, diethyl ether, ethylene glycol monomethyl ether, ethylene glycol monoethyl ether and 1-methoxy-2-propanol; dimethylformamide, dimethylacetamide, dimethylsulfoxide and sulfolane. These may be used alone or in combination of two or more. The publicly known surfactant may also be added.

Subsequently, the photosensitive transfer sheet can be produced by applying the photosensitive composition solution on the support and drying to form the photosensitive layer.

The method for applying the photosensitive composition solution is not particularly limited, can be appropriately selected depending on the purpose, and includes, for example, a spray method, a roll coating method, a rotation application method, a slit coating method, an extrusion coating method, a curtain coating method, a die coating method, a gravure coating method, a wire bar coating method and a knife coating method.

A condition for the drying varies depending on each ingredient, a type of the solvent and a ratio to be used, and is typically the drying at 60° C. to 110° C. for about 30 seconds to 15 minutes The photosensitive composition of the present invention can enhance the sensitivity by comprising the titanocene based compound of the present invention as the photopolymerization initiator. Therefore, it can be used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs), and pattern forming materials.

(Pattern Forming Method)

The pattern forming method is not particularly limited, and steps performed upon ordinary pattern formation can be appropriately selected depending on the purpose. For example, a laminated body forming step, an exposing step, a developing step, an etching step and a plating step are included.

—Laminated Body Forming Step—

The laminated body forming step is a step of forming a laminated body by laminating the photosensitive layer of the photosensitive transfer sheet of the present invention on the substrate.

—Substrate—

The substrate is a substrate to be treated onto which the photosensitive layer is formed or a body to be transferred onto which at least the photosensitive layer in the photosensitive transfer sheet of the present invention is transferred, and is not particularly limited, can be appropriately selected depending on the purpose, and for example, can be optionally selected from those having high surface smoothness to those having the surface with asperity. A platy substrate is preferable, and a so-called substrate is used. Specifically, publicly known substrates, glass plates (soda glass plates), synthetic resin films, papers and metal plates for producing the printed wiring boards are included.

The method for forming the laminated body is not particularly limited as long as the laminated body is formed by laminating the photosensitive layer on the substrate, and includes, for example, the method of laminating by transferring at least the photosensitive layer in the photosensitive transfer sheet of the present invention with performing at least either heating or pressurizing.

More specifically, the photosensitive transfer sheet of the present invention is laminated on the surface of the substrate with performing at least either heating or pressurizing. When the photosensitive transfer sheet has the protection film, it is preferable that the protection film is peeled and the lamination is performed so that the photosensitive layer is overlaid on the substrate.

A heated temperature is not particularly limited, can be appropriately selected depending on the purpose, and for example is preferably 15° C. to 180° C. and more preferably 60° C. to 140° C.

A pressurized pressure is not particularly limited, can be appropriately selected depending on the purpose, and for example is preferably 0.1 MPa to 1.0 MPa and more preferably 0.2 MPa to 0.8 MPa.

An apparatus for performing at least either the heating is not particularly limited, can be appropriately selected depending on the purpose, and for example, suitably includes a laminator (VP-II supplied from Taisei Laminator Co., Ltd.).

—Exposing Step—

The exposing step is a step of exposing to the photosensitive layer in the photosensitive transfer sheet of the present invention.

The exposure is not particularly limited, can be appropriately selected depending on the purpose, and includes digital exposure and analog exposure. The exposure through step wedge (e.g., Fuji Step Guide supplied from Fuji Photo Film Co., Ltd.) is preferable.

An energy amount of light upon the exposure is preferably 5 mJ/cm$^2$ to 300 mJ/cm$^2$, more preferably 5 mJ/cm$^2$ to 100 mJ/cm$^2$, and particularly preferably 5 mJ/cm$^2$ to 50 mJ/cm$^2$. When the exposure amount is less than 5 mJ/cm$^2$, the exposure is insufficient, and when it exceeds 300 mJ/cm$^2$, an irradiation time is increased and the productivity is sometimes reduced.

A light source upon the exposure is not particularly limited, can be appropriately selected depending on the purpose, and includes, for example, an ultrahigh pressure mercury lamp, a xenon lamp, a carbon arc lamp, a halogen lamp, a fluorescence tube for copy machines, LED, and laser light (semiconductor laser, solid laser, liquid laser, gas laser). Among them, the ultrahigh pressure mercury lamp and the laser light are preferable, and the laser light is more preferable in terms of being capable of performing on/off control of the light within a short time and easy interference control of the light.

A wavelength of the light source is not particularly limited, and can be appropriately selected depending on the purpose. For example, as the ultrahigh pressure mercury lamp, i-ray (365 nm) is preferable, and as the solid laser, YAG-SHG solid laser (532 nm), semiconductor excitation solid laser (532 nm, 355 nm, 266 nm) are preferable. As the gas laser, KrF laser (249 nm) and ArF laser (193 nm) are preferable.

—Developing Step—

The developing step is a step of developing by removing an uncured region on the photosensitive layer to form a pattern after the exposing step.

The developing step can be suitably carried out by, for example, a developing unit.

The developing unit is not particularly limited as long as the development can be performed using a developer, can be appropriately selected depending on the purpose, and includes, for example, a unit of spraying the developer, a unit of applying the developer, and a unit of immersing in the developer. These may be used alone or in combination of two or more.

The developing unit may have a developer exchanging unit of exchanging the developer and a developer supplying unit of supplying the developer.

The developer is not particularly limited, and can be appropriately selected depending on the purpose, and includes, for example, an alkaline solution, a water-based developer and an organic solvent. Among them, a weak alkaline aqueous solution is preferable. A basic component in the weak alkaline solution includes, for example, lithium hydroxide, sodium hydroxide, potassium hydroxide, lithium carbonate, sodium carbonate, potassium carbonate, lithium hydrogen carbonate, sodium hydrogen carbonate, potassium hydrogen carbonate, sodium phosphate, potassium phosphate, sodium pyrophosphate potassium pyrophosphate and borax.

A pH value of the weak alkaline aqueous solution is preferably about 8 to 12 and more preferably about 9 to 11. The weak alkaline aqueous solution includes, for example, an aqueous solution of 0.1% by mass to 5% by mass sodium carbonate or potassium carbonate.

The temperature of the developer can be appropriately selected depending on the developing property of the photosensitive layer, and is preferably about 25° C. to 40° C.

The developer may be combined with the surfactant, the anti-foaming agent, organic solvents (e.g., ethylenediamine, ethanolamine, tetramethylammonium hydroxide, diethylenetriamine, triethylene pentamine, morpholine, triethanolamine), and organic solvents (e.g., alcohols, ketones, esters, ethers, amides lactones) for accelerating the development. The developer may also be a water based developer obtained by mixing water or the alkaline aqueous solution with the organic solvent, or may also be the organic solvent alone.

—Etching Step—

The etching step can be performed by the method appropriately selected from publicly known etching treatment methods.

An etching solution used for the etching treatment is not particularly limited, and can be appropriately selected depending on the purpose, and includes, for example, a cupric chloride solution, a ferric chloride solution, an alkali etching solution and a hydrogen peroxide based etching solution when the metal layer is formed of copper. Among them, the ferric chloride solution is preferable in terms of etching factor. A publicly known sand blast method can also be used.

By giving the etching treatment in the etching step and subsequently removing the pattern, it is possible to form a wiring pattern (circuit) on the surface of the substrate.

—Plating Step—

The plating step can be performed by the method appropriately selected from publicly known plating treatment methods.

The plating treatment includes, for example, copper plating such as copper sulfate plating and copper pyrophosphate plating, solder plating such as high throw solder plating, nickel plating such as Watt bath (nickel sulfate-nickel chloride) plating and nickel sulfaminate plating, and gold plating such as hard gold plating and soft gold plating.

By giving the plating treatment in the plating step and subsequently removing the pattern, and further removing an unnecessary region by resist peeling as needed, it is possible to form the metal wiring pattern (circuit) on the surface of the substrate.

(Method for Producing Printed Wiring Board)

The pattern forming method can be used suitably for producing the printed wiring board, particularly producing the printed wiring board having a hole section such as a through hole or a via hole. Hereinafter, one example of the method for producing the printed wiring board taking the pattern forming method of the present invention will be described.

In the producing the printed wiring board having the hole section such as through holes or via holes, (1) the photosensitive transfer sheet is laminated to form the laminated body on the substrate for forming the printed wiring board having the hole section as the substrate so that the photosensitive layer is at the side of the substrate, (2) the light is irradiated from an opposed side to the substrate of the laminated body to the desired region to cure the photosensitive layer, (3) the support in the photosensitive transfer sheet is removed from the laminated body, and (4) the pattern can be formed by developing the photosensitive layer and removing the uncured region in the laminated body.

The removal of the support in the above (3) may be performed between (1) and (2) instead of performing between (2) and (4).

Subsequently to obtain the printed wiring board, the substrate for the printed wiring board could be treated by the etching treatment or the plating treatment (e.g., publicly known subtractive or additive method, e.g., semi-additive method, full-additive method). Among them, the subtractive method is preferable in order to form the printed wiring board by tenting which is industrially advantageous. A residual cured resin on the substrate for forming the printed wiring board after the above treatment is peeled. In the semi-additive method, by further etching a copper thin membrane after peeling, it is possible to produce the desired printed wiring board. It is also possible to produce the multilayer printed wiring board in the same way as in the method for producing the above printed wiring board.

EXAMPLES

Examples of the present invention will be described below, but the present invention is not limited thereto at all.

Synthesis Example 1

—Production of Exemplified Compound A-1—

(1) Preparation of 1-(1,1-dimethoxyethyl)-2,4-difluorobenzene

In a solution composed of 15.7 g of 2,4-difluoroacetophenone, 35 g of trimethyl ortho-formate and 15 g of methanol, 0.96g of p-toluenesulfonic acid was added, and reacted at 40° C. to 45° C. for 2 hours. This was added to an aqueous solution of 5% by mass sodium hydrogen carbonate, which was then extracted with ethyl acetate. An extract was washed with water, and dried on $Na_2SO_4$. Then, ethyl acetate was concentrated to yield 18.2 g of 1-(1,1-dimethoxyethyl)-2,4-difluorobenzene. It was confirmed that the 1-(1,1-dimethoxyethyl)-2,4-difluorobenzene had NMR data of ($CDCl_3$, δppm) 1.62 (s, 3H), 3.9 (s, 6H), 6.74-6.9 (m, 2H), 7.56-7.7 (m, 1H) by NMR (supplied from Varian Technologies Japan Limited).

(2) Preparation of dicyclopentadienyl-bis{2,6-difluoro-3-(1,1-dimethoxyethyl)phenyl}titanium 1-(1,1-Dimethoxyethyl)-2,4-difluorobenzene (8.5 g) was dissolved in 130 mL of diethyl ether, and cooled to −70° C. under nitrogen gas flow. Then, 21.5 g of a solution of 15% by mass n-butyl lithium in hexane was added thereto over 10 minutes, and stirred at this temperature for 3 hours. Subsequently, 5.0 g of dicyclopentanedienyl titanium dichloride was added thereto, and stirred at this temperature for 30 minutes, then warmed up to room temperature, and stirred at room temperature for 6 hours.

A precipitated precipitate was collected by filtration. This was dissolved in chloroform, insoluble matters were removed by filtration, and the solution was concentrated under reduced pressure. A residue was crystallized with ethyl acetate to yield 4.7 g of a golden yellow crystal. A melting point of this crystal was 165° C. to 167° C.

The product was analyzed by the NMR, and the data of ($CDCl_3$, δppm) 1.45-1.64 (m, 6H), 3.1-3.25 (m, 12H), 6.3-6.55 (m, 2H), 6.45 (s, 10H), 7.2-7.37 (m, 2H) were obtained, confirming that the yielded crystal was dicyclopentadienyl-bis{2,6-difluoro-3-(1,1-dimethoxyethyl)phenyl}titanium.

(3) Preparation of dicyclopentadienyl-bis{(2,6-difluoro-3-acetyl)phenyl)titanium (Exemplified Compound A-1)

Dicyclopentadienyl-bis{2,6-difluoro-3-(1,1-dimethoxyethyl)phenyl}titanium (3.0 g) was added to a mixed solution of 4 mL of water, 16 mL of glacial acetic acid and 20 mL of ethyl acetate, and stirred at room temperature for one hour. The reaction mixture was added to an aqueous solution of 5% by mass sodium hydrogen carbonate, which was then extracted with ethyl acetate.

A resulting extract was washed with water and dried on $Na_2SO_4$. Ethyl acetate was concentrated under reduced pressure. Ethanol was added to a residue to crystallize to yield 2.0 g of a golden yellow crystal. The melting point of this crystal was 205° C. to 207° C.

The product was analyzed by the NMR, and the data of ($CDCl_3$, δppm) 2.3-2.65 (m, 6H), 6.3-6.65 (m, 2H), 6.5 (s, 10H), 7.45-7.65 (m, 2H) were obtained, confirming that the yielded crystal was dicyclopentadienyl-bis{(2,6-difluoro-3-acetyl)phenyl)titanium (exemplified compound A-1).

Synthesis Example 2

—Production of Exemplified Compound A-2—

The compound was produced using 2,4-difluoropropiophenone by the same procedure as in the production of the exemplified compound A-1.

It was confirmed that the exemplified compound A-2 had the NMR data of (CDCl$_3$, $\delta$ppm) 0.95-1.30 (m, 6H), 2.6-3.0 (m, 4H), 6.38-6.75 (m, 2H), 6.48 (s, 10H), 7.48-7.6 (m, 2H).

Synthesis Example 3

—Production of Exemplified Compound A-30—

(1) Preliminary Step i) Preparation of 4-bromo-2',4'-difluorobutyrophenone

4-Bromo-2',4'-difluorobutyrophennone was prepared using 1,3-difluorobenzene, 4-bromobutyroyl chloride and aluminium chloride based on Bartroli J. et al., J. Org. Chem., 60:3000, 1995.

It was confirmed that the 4-bromo-2',4'-difluorobutyrophenone had the NMR data of (CDCl$_3$, $\delta$ppm) 2.25-2.35 (m, 2H), 3.13-3.20 (m, 2H), 6.85-7.03 (m, 2H), 7.92-8.00 (m, 1H).

ii) Preparation of 2-(2',4'-difluorophenyl)-2-(3"-bromopropyl)-1,3-dioxolane 4-Bromo-2',4'-difluorobutyrophenone (22 g), 13.3 g of trimethyl ortho-formate, 25.9 g of ethylene glycol and 1.6 g of p-toluenesulfonic acid were mixed, and heated and reacted at 80° C. to 100° C. The reaction solution was added to the aqueous solution of 5% by mass NaHCO$_3$, which was then extracted with ethyl acetate. An extract was washed with water, dried on Na$_2$SO$_4$, and ethyl acetate was concentrated under reduced pressure to yield 25.3 g of 2-(2',4'-difluorophenyl)-2-(3"-bromopropyl)-1,3-dioxolane.

It was confirmed that the 2-(2',4'-difluorophenyl)-2-(3"-bromopropyl)-1,3-dioxolane had the NMR data of (CDCl$_3$, $\delta$ppm) 1.88-1.98 (m, 2H), 2.15-2.20 (m, 2H), 3.38-3.43 (m, 2H), 3.80-3.90 (m, 2H), 6.76-6.90 (m, 2H), 7.40-7.52 (m, 1H).

iii) Preparation of 2-(2',4'-difluorophenyl)-2-(3"-methoxypropyl)-1,3-dioxolane 2-(2',4'-difluorophenyl)-2-(3"-bromopropyl)-1,3-dioxolane (24.9 g) was dissolved in 20 mL of methanol, 30 g of a solution of 28% by mass sodium methoxide in methanol was added thereto, which was then reacted at 50° C. to 55° C. Water was added to the reaction solution, which was extracted with ethyl acetate. An extract was washed with water, dried on Na$_2$SO$_4$, and ethyl acetate was concentrated under reduced pressure to yield an oily product. This was purified by silica gel chromatography (hexane:ethyl acetate=7:3 (volume ratio) was used as an eluant) to yield 13.7 g of 2-(2',4'-difluorophenyl)-2-(3"-methoxypropyl)-1,3-dioxolane.

It was confirmed that the 2-(2',4'-difluorophenyl)-2-(3"-methoxypropyl)-1,3-dioxolane had the NMR data of (CDCl$_3$, $\delta$ppm) 1.57-1.68 (m, 2H), 2.05-2.12 (m, 2H), 3.30 (s, 3H), 3.33-3.39 (m, 2H), 3.80-3.88 (m, 2H), 4.04-4.10 (m, 2H), 6.76-6.86 (m, 2H), 7.40-7.52 (m, 1H).

iv) Preparation of 4-methoxy-2',4'-difluorobutyrophenone 2-(2',4'-Difluorophenyl)-2-(3"-methoxypropyl)-1,3-dioxolane (13.4 g), 0.46 mL of hydrochloric acid, 17 mL of water and 34 mL of methanol were heated and stirred at 50° C. to 55° C. for about 6 hours, then 100 mL of water added thereto to cool, and a precipitated crystal was filtrate to yield 10.9 g of 4-methoxy-2',4'-difluorobutyrophenone. The melting point of the resulting 4-methoxy-2',4'-difluorobutyrophenone was 42° C. to 44° C.

It was confirmed that the 4-methoxy-2',4'-difluorobutyrophenone had the NMR data of CDCl$_3$, $\delta$ppm) 1.96-2.06 (m, 2H), 3.00-3.08 (m, 2H), 3.34 (s, 3H), 3.44-3.48 (m, 2H), 6.84-7.00 (m, 2H), 7.88-7.97 (m, 1H).

(2) Preparation of 1',1',4'-trimethoxybutyl-2,4-difluorobenzene

4-Methoxy-2',4'-difluorobutyrophenone (10.7 g), 32 g of trimethyl ortho-formate, 4.8 g of methanol and 0.5 g of p-toluenesulfonic acid were mixed, and heated and reacted at 45° C. The reaction solution was added to the aqueous solution of 5% by mass NaHCO$_3$, which was then extracted with ethyl acetate. An extract was washed with water, dried on Na$_2$SO$_4$, and ethyl acetate was concentrated under reduced pressure to yield 13 g of 1',1',4'-trimethoxybutyl-2,4-difluorobenzene.

It was confirmed that the 1',1',4'-trimethoxybutyl-2,4-difluorobenzene had the NMR data of CDCl$_3$, $\delta$ppm) 1.20-1.32 (m, 2H), 2.06-2.10 (m, 2H), 3.17 (s, 3H), 3.25 (s, 3H), 3.22-3.28 (m, 2H), 6.74-6.90 (m, 2H), 7.55-7.65(m, 1H).

(3) Preparation of cyclopentadienyl-bis{3-(1',1'-4'-trimethoxybutyl)-2,6-difluorophenyl}titanium Under the nitrogen gas flow, 10.9 g of 1',1',4'-trimethoxybutyl-2,4-difluorobenzene was dissolved in 130 mL of diethyl ether, and cooled to −70° C. Then, 21.5 g of 15% by mass n-butyl lithium in hexane was added thereto over 10 minutes, and stirred at that temperature for 6 hours. Subsequently, 5.0 g of dicyclopentadienyl titanium dichloride was added thereto, stirred at that temperature for one hour, then gradually warmed up to room temperature, and stirred at room temperature for 6 hours. The solvent was concentrated under reduced pressure. A residue was dissolved in chloroform, and insoluble matters were removed by filtration. A filtrate was concentrated under reduced pressure, and a residue was purified by silica gel chromatography (chloroform containing 1% by volume triethylamine: ethyl acetate=8:2 (volume ratio) was used as the eluant) to yield 3.5 g of dicyclopentadienyl-bis{3-(1',1',4'-trimethoxybutyl)-2,6-difluorophenyl}titanium.

It was confirmed that the dicyclopentadienyl-bis{3-(1',1', 4'-trimethoxybutyl)-2,6-difluorophenyl}titanium had the NMR data of (CDCl$_3$, $\delta$ppm) 1.16-1.40 (m, 4H), 1.90-2.15 (m, 4H), 3.08-3.35 (m, 22H), 6.34-6.55 (m, 2H), 6.42 (s, 10H), 7.2-7.35 (m, 2H).

(4) Preparation of dicyclopentadienyl-bis{3-(4'-methoxybutyryl)-2,6-difluorophenyl}titanium (compound A-30)

Dicyclopentadienyl-bis{3-(1',1',4'-trimethoxybutyl)-2,6-difluorophenyl}titanium (4.2 g), 20 mL of 50% by mass hydrous acetic acid and 40 mL of methanol were stirred at room temperature for 6 hours. The reaction solution was neutralized by adding the aqueous solution of 5% by mass NaHCO$_3$, and extracted with ethyl acetate. An extract was washed with water, and dried on Na$_2$SO$_4$. Ethyl acetate was concentrated under reduced pressure. This was purified by silica gel chromatography (chloroform containing 1% by volume triethylamine:ethyl acetate=8:2 (volume ratio) was used as the eluant) to yield 1.4 g of dicyclopentadienyl-bis{3-(4'-methoxybutyryl)-2,6-difluorophenyl}titanium (compound A-30).

It was confirmed that the dicyclopentadienyl-bis{3-(4'-methoxybutyryl)-2,6-difluorophenyl}titanium (compound A-30) had the NMR data of (CDCl$_3$, δppm) 1.84-2.06 (m, 4H), 2.76-3.55 (m, 14H), 6.38-6.65 (m, 2H), 6.50 (s, 10H), 7.48-7.60 (m, 2H).

Synthesis Example 4

—Production of Exemplified Compound A-3—

The compound A-3 was produced using 2,4-difluorovalerophenone synthesized as was the case with the exemplified compound A-30 in the same procedure as in the production of the exemplified compound A-1.

The exemplified compound A-3 was confirmed to have the NMR Data of (CDCl$_3$, δppm) 0.75-1.00 (m, 6H), 1.18-1.5 (m, 4H), 1.5-1.75 (m, 4H), 2.6-2.94 (m, 4H), 6.28-6.68 (m, 2H), 6.48 (s, 10H), 7.44-7.6 (m, 2H).

Synthesis Example 5

—Production of Exemplified Compound A-4—

The compound A-4 was produced using 2,4-difluorophenylpentyl ketone synthesized as was the case with the exemplified compound A-30 in the same procedure as in the production of the exemplified compound A-1.

The exemplified compound A-4 was confirmed to have the NMR data of CDCl$_3$, δppm) 0.75-0.97 (m, 6H), 1.05-1.42 (m, 4H), 1.5-1.75 (m, 4H), 2.6-2.94 (m, 4H), 6.38-6.7 (m, 2H), 6.48 (s, 10H), 7.44-7.6 (m, 2H).

Example 1

—Formation of Photosensitive Layer—

A photosensitive composition solution composed of the following composition was applied onto a polyethylene terephthalate film with a thickness of 20 μm as a support, and dried to form a photosensitive layer with a thickness of 30 μm.

<Composition of photosensitive resin composition solution>

| | |
|---|---|
| Methyl methacrylate/2-ethylhexyl acrylate/benzyl methacrylate/methacrylic acid copolymer (copolymer composition [molar ratio]: 55/11.7/4.5/28.8, mass average molecular weight 90,000) | 15 parts by mass |
| Dodecapropylene glycol diacrylate | 6.5 parts by mass |
| Tetraethylene glycol dimethacrylate | 1.5 parts by mass |
| Exemplified compound A-1 | 1.04 parts by mass |

-continued

<Composition of photosensitive resin composition solution>

| | |
|---|---|
| p-Toluenesulfonamide | 0.5 parts by mass |
| 3-Morpholinomethyl-1-phenyltriazole-2-thione | 0.01 parts by mass |
| Leuco crystal violet | 0.2 parts by mass |
| Tribromomethylphenylsulfone | 0.1 parts by mass |
| Methyl ethyl ketone | 30 parts by mass |

—Production of Photosensitive Transfer Sheet—

A polyethylene film with a thickness of 20 μm was laminated on the above photosensitive layer to obtain a photosensitive transfer sheet.

—Measurement of Sensitivity—

The photosensitive transfer sheet from which the protection film had been peeled was overlaid on a copper-clad laminate (copper-clad laminate R-701 for National printed wiring substrate supplied from Matsushita Electric Works, Ltd.) whose surface had been polished, washed with water and dried so that the copper surface was contacted with the photosensitive layer, and laminated using a laminator (MODEL 8B-720-PH supplied from Taisei Laminator Co., Ltd.). A condition for lamination was set to a substrate temperature at 70° C., a lamination temperature at 105° C., a lamination pressure at 3 kg/cm$^2$, and a feeding speed of the laminate at 1.2 m/minute. After the lamination, the laminated body was left stand at a temperature of 23° C. and a relative humidity of 55% for 10 minutes. Through step wedge (e.g., Fuji Step Guide supplied from Fuji Film Co., Ltd.) having a density phase difference of 0.15 and 1 to 15 of density phases, laser light of 532 nm at 40 mJ/cm$^2$ was irradiated to the photosensitive layer in the photosensitive transfer sheet from the side of the polyethylene terephthalate film (support) using a laser exposure apparatus. Subsequently, the polyethylene terephthalate film was peeled out, and an aqueous solution of 1% by mass sodium carbonate at 30° C. was sprayed onto the surface of the photosensitive layer at a pressure of 1.03 kg/cm$^2$ to remove an unexposed region and develop. After the development, a minimum number (clear column number) of the phases (cleared phase number) where the photosensitive layer was completely dissolved was read out. The higher cleared phase number means the higher sensitivity. Results are shown in Table 1.

Example 2

A photosensitive transfer sheet was made and its sensitivity was measured in the same way as in Example 1, except that the exemplified compound A-2 was used in place of the exemplified compound A-1. The result of the measured sensitivity is shown in Table 1.

Example 3

A photosensitive transfer sheet was made and its sensitivity was measured in the same way as in Example 1, except that the exemplified compound A-3 was used
in place of the exemplified compound A-1. The result of the measured sensitivity is shown in Table 1.

Example 4

A photosensitive transfer sheet was made and its sensitivity was measured in the same way as in Example 1, except that the exemplified compound A-4 was used in place of the exemplified compound A-1. The result of the measured sensitivity is shown in Table 1.

Example 5

A photosensitive transfer sheet was made and its sensitivity was measured in the same way as in Example 1, except that the exemplified compound A-30 was used in place of the exemplified compound A-1. The result of the measured sensitivity is shown in Table 1.

Comparative Example 1

A photosensitive transfer sheet was made and its sensitivity was measured in the same way as in Example 1, except that the comparative compound B-1 (Irgacure 784 supplied from Ciba Specialty Chemicals) represented by the following structural formula was used in place of the exemplified compound A-1. The result of the measured sensitivity is shown in Table 1.

TABLE 1 comparative compound B-1

| | Exemplified compound | Sensitivity (Clear column) |
|---|---|---|
| Example 1 | A-1 | 14 |
| Example 2 | A-2 | 14 |
| Example 3 | A-3 | 14 |
| Example 4 | A-4 | 14 |
| Example 5 | A-30 | 14 |
| Comparative Example 1 | Comparative compound B-1 | 10 |

From the results in Table 1, it has been found that the photosensitive transfer sheets in Examples 1 to 5 using the photosensitive composition containing the titanocene based compound of the present invention have the higher sensitivity than the photosensitive transfer sheet in Comparative Example 1 using the photosensitive composition containing no titanocene based compound.

The titanocene based compound of the present invention can be suitably used as the photopolymerization initiator in the photosensitive composition used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs), and pattern forming materials, and particularly can be used suitably for the photosensitive composition of the present invention.

The photosensitive composition of the present invention can enhance the sensitivity by containing the titanocene based compound of the present invention as the photopolymerization initiator. Therefore, the photosensitive composition can be widely used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs), and pattern forming materials, and particularly can be used suitably for the photosensitive transfer sheet of the present invention.

The photosensitive transfer sheet of the present invention can enhance the sensitivity by using the photosensitive composition containing the titanocene based compound as the photopolymerization initiator. Therefore, the photosensitive transfer sheet can be widely used in the fields of printed wiring boards, lead frames, semiconductor packages, members for displays (e.g., color filters, pillar materials, rib materials, spacers, partition walls), three dimensional optical moldings, image forming materials (e.g., printing matrices, proofs), and pattern forming materials.

What is claimed is:

1. A titanocene based compound characterized by being represented by the following general formula (I):

general formula (I)

wherein $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II):

general formula (II)

$$\underset{R_3}{\overset{O}{\|}}$$

where $R_3$ represents any of a hydrogen atom, and alkyl, alkenyl, cycloalkyl, aryl and aralkyl groups which may have substituents, or may be bound to an aromatic ring to form a 5-membered or 6-membered condensed ring containing a carbonyl group.

2. A titanocene based compound characterized by being represented by the following general formula (III):

general formula (III)

wherein $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_3$ and $Ar_4$ each independently represents any of 6-memberd carbocyclic, 5-membered heterocyclic and 6-membered heterocyclic aromatic rings, wherein at least one of positions other than a position of the carbon atom bound to Ti has been substituted with a group represented by the following general formula (IV):

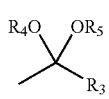

general formula (IV)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group; $R_4$ and $R_5$ each independently represents alkyl groups having 1 to 5 carbon atoms, or are linked one another to form either a 5-membered ring or a 6-membered ring.

3. The titanocene based compound according to claim 1, wherein $R_1$ and $R_2$ are any of cyclopentadienyl, methylcyclopentadienyl and pentamethylcyclopentadienyl groups.

4. The titanocene based compound according to claim 2, wherein $R_1$ and $R_2$ are any of cyclopentadienyl, methylcyclopentadienyl and pentamethylcyclopentadienyl groups.

5. The titanocene based compound according to claim 1, wherein $Ar_1$ and $Ar_2$ are the same group.

6. The titanocene based compound according to claim 2, wherein $Ar_3$ and $Ar_4$ are the same group.

7. The titanocene based compound according to claim 1, wherein at least one of ortho positions for a carbon bond with Ti in $Ar_1$ has been substituted with a fluorine atom.

8. The titanocene based compound according to claim 2, wherein at least one of ortho positions for a carbon bond with Ti in $Ar_3$ has been substituted with a fluorine atom.

9. The titanocene based compound according to claim 7, wherein $R_1$ and $R_2$ are selected from a cyclopentadienyl group and a cyclopentadienyl group substituted with an alkyl group having 1 to 6 carbon atoms, and $Ar_1$ and $Ar_2$ are represented by the following general formula (V):

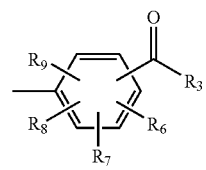

general formula (V)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group; and $R_6$, $R_7$, $R_8$ and $R_9$ each independently represents any of hydrogen atoms or fluorine atoms.

10. The titanocene based compound according to claim 8, wherein $R_1$ and $R_2$ are selected from a cyclopentadienyl group and a cyclopentadienyl group substituted with an alkyl group having 1 to 6 carbon atoms, and $Ar_3$ and $Ar_4$ are represented by the following general formula (V):

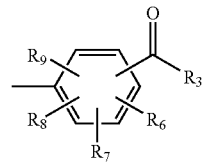

general formula (V)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group; and $R_6$, $R_7$, $R_8$ and $R_9$ each independently represents any of hydrogen atoms or fluorine atoms.

11. The titanocene based compound according to claim 9, wherein a carbonyl group has been bound to either a meta position or a para position for the carbon atom bound to Ti.

12. The titanocene based compound according to claim 10, wherein a carbonyl group has been bound to either a meta position or a para position for the carbon atom bound to Ti.

13. The titanocene based compound according to claim 1, wherein the compound represented by the general formula (I) is obtained using the compound represented by the following general formula (III):

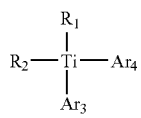

general formula (III)

where $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_3$ and $Ar_4$ each independently represents any of 6-memberd carbocyclic, 5-membered heterocyclic and 6-membered heterocyclic aromatic rings, wherein at least one of positions other than a position of the carbon atom bound to Ti has been substituted with a group represented by the following general formula (IV):

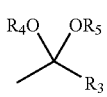

general formula (IV)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group; $R_4$ and $R_5$ each independently represents alkyl groups having 1 to 5 carbon atoms, or are linked one another to form either a 5-membered ring or a 6-membered ring.

14. The titanocene based compound according to claim 2, wherein the compound represented by the general formula (III) is obtained by reacting a compound represented by the following formula (VI) with a compound represented by either the following general formula (VII) or (VIII):

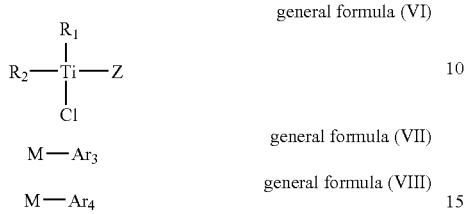

general formula (VI)

general formula (VII)

general formula (VIII)

where $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_3$ and $Ar_4$ each independently represents any of 6-memberd carbocyclic, 5-membered heterocyclic and 6-membered heterocyclic aromatic rings, wherein at least one of positions other than a position of the carbon atom bound to Ti has been substituted with a group represented by the following general formula (IV):

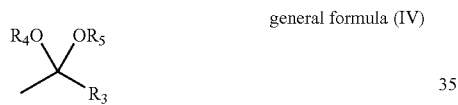

general formula (IV)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group; $R_4$ and $R_5$ each independently represents alkyl groups having 1 to 5 carbon atoms, or are linked one another to form either a 5-membered ring or a 6-membered ring; M represents any of Li, MgCl, MgBr and MgI; and Z represents any halogen atom of Cl, Be or I.

15. A photosensitive composition, comprising:
a binder,
a polymerizable compound, and
a titanocene based compound,
wherein the titanocene based compound is represented by the following general formula (I):

general formula (I)

where $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II):

general formula (II)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group.

16. A photosensitive transfer sheet, comprising:
a support, and
a photosensitive layer composed of a photosensitive composition on the support,
wherein the photosensitive composition comprises a binder, a polymerizable compound, and a titanocene based compound,
where the titanocene based compound is represented by the following general formula (I):

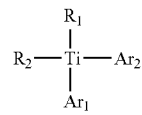

general formula (I)

where $R_1$ and $R_2$ each independently represents any of cyclopentadienyl, indenyl and tetrahydroindenyl groups which may have substituents, or may be linked one another via a bivalent linking group X; X represents any of a direct bond, an oxygen atom and a sulfur atom, or represents any of chain or cyclic alkylene, alkylidene and arylene which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II):

general formula (II)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group.

17. The photosensitive transfer sheet according to claim 16, wherein the photosensitive transfer sheet has a protection film on the photosensitive layer.

18. The photosensitive transfer sheet according to claim 16, wherein a thickness of the photosensitive layer is 1 μm to 100 μm.

19. A pattern forming method, comprising:
laminating a photosensitive layer of a photosensitive transfer sheet on a substrate to form a laminated body,
exposing the photosensitive layer, and
developing the photosensitive layer,
wherein the photosensitive transfer sheet comprises a support, and a photosensitive layer composed of a photosensitive composition on the support; the photosensitive composition comprises a binder, a polymerizable compound, and a titanocene based compound; the titanocene based compound is represented by the following general formula (I):

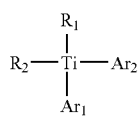

general formula (I)

where $R_1$ and $R_2$ each independently represents any of cyclopentadienyl, indenyl and tetrahydroindenyl groups which may have substituents, or may be linked one another via a bivalent linking groups X; X represents any of a direct bond, an oxygen atom and a sulfur atom, or represents any of chain or cyclic alkylene, alkylidene and arylene which may contain heteroatoms; $Ar_1$ and $Ar_2$ each independently represents any of 6-membered carbocyclic, 5-membered heterocyclic and 6-membered heterocyclic aromatic rings where at least one position other than a carbon bond with Ti has been substituted with a group represented by the following general formula (II):

general formula (II)

where $R_3$ represents any of a hydrogen atom, and alkyl, alkenyl, cycloalkyl, aryl and aralkyl groups which may have substituents, or may be bound to an aromatic ring to form a 5-memberd or 6-membered condensed ring containing a carbonyl group.

20. The pattern forming method according to claim 19, wherein the exposing is performed through step wedge.

* * * * *